United States Patent
Kalgutkar

(10) Patent No.: US 7,297,724 B2
(45) Date of Patent: *Nov. 20, 2007

(54) PHOTOINIATORS HAVING TRIARYLSULFONIUM AND ARYLSULFINATE IONS

(75) Inventor: Rajdeep S. Kalgutkar, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/275,831

(22) Filed: Jan. 31, 2006

(65) Prior Publication Data

US 2006/0111463 A1   May 25, 2006

Related U.S. Application Data

(63) Continuation of application No. 10/672,554, filed on Sep. 26, 2003, now Pat. No. 7,026,367.

(51) Int. Cl.
C08F 2/46 (2006.01)

(52) U.S. Cl. .................. 522/31; 522/182

(58) Field of Classification Search ............. 522/25, 522/26, 59, 31, 182
See application file for complete search history.

(56) References Cited

U.S. PATENT DOCUMENTS

| | | | |
|---|---|---|---|
| 3,556,794 A | 1/1971 | Margerum | |
| 3,573,922 A | 4/1971 | Rust | |
| 3,607,272 A | 9/1971 | Rust | |
| 3,623,875 A | 11/1971 | Desjarlais | |
| 3,627,656 A | 12/1971 | Miller et al. | |
| 3,642,487 A | 2/1972 | Rust | |
| 3,708,296 A | 1/1973 | Schlesinger | |
| 3,729,313 A | 4/1973 | Smith | |
| 3,741,769 A | 6/1973 | Smith | |
| 3,788,858 A | 1/1974 | Margerum | |
| 3,808,006 A | 4/1974 | Smith | |
| 4,069,054 A | 1/1978 | Smith | |
| 4,069,055 A | 1/1978 | Crivello | |
| 4,182,035 A | 1/1980 | Yamauchi et al. | |
| 4,216,288 A | 8/1980 | Crivello | |
| 4,250,053 A | 2/1981 | Smith | |
| 4,250,311 A | 2/1981 | Crivello | |
| 4,257,915 A | 3/1981 | Eaton | |
| 4,259,075 A | 3/1981 | Yamauchi et al. | |
| 4,356,296 A | 10/1982 | Griffith et al. | |
| 4,366,228 A | 12/1982 | Specht et al. | |
| 4,394,403 A | 7/1983 | Smith | |
| 4,455,147 A | 6/1984 | Lewis et al. | |
| 4,499,251 A | 2/1985 | Omura et al. | |
| 4,503,169 A | 3/1985 | Randklev | |
| 4,537,940 A | 8/1985 | Omura et al. | |
| 4,539,382 A | 9/1985 | Omura et al. | |
| 4,642,126 A | 2/1987 | Zador et al. | |
| 4,650,913 A | 3/1987 | Feiring | |
| 4,652,274 A | 3/1987 | Boettcher et al. | |
| 4,665,217 A | 5/1987 | Reiners et al. | |
| 4,695,251 A | 9/1987 | Randklev | |
| 4,752,338 A | 6/1988 | Reiners et al. | |
| 4,755,620 A * | 7/1988 | Iwamoto et al. ............. 560/224 |
| 4,859,572 A * | 8/1989 | Farid et al. .............. 430/281.1 |
| 4,871,786 A | 10/1989 | Aasen et al. | |
| 4,872,936 A | 10/1989 | Engelbrecht | |
| 4,908,227 A | 3/1990 | Dougherty et al. | |
| 4,959,297 A | 9/1990 | Palazzotto | |
| 4,966,934 A * | 10/1990 | Huang et al. ............... 524/315 |
| 4,971,892 A * | 11/1990 | Ali et al. .................. 430/281.1 |
| 4,983,644 A * | 1/1991 | Mukai et al. .................. 522/14 |
| 5,076,844 A | 12/1991 | Fock et al. | |
| 5,084,586 A | 1/1992 | Farooq | |
| 5,089,374 A | 2/1992 | Saeva | |
| 5,105,006 A * | 4/1992 | Parker .......................... 562/30 |
| 5,124,417 A | 6/1992 | Farooq | |
| 5,130,347 A | 7/1992 | Mitra | |
| 5,154,762 A | 10/1992 | Mitra et al. | |
| 5,256,447 A | 10/1993 | Oxman et al. | |
| 5,304,585 A * | 4/1994 | Bunker ....................... 523/116 |
| 5,486,544 A * | 1/1996 | Kawashima et al. .......... 522/17 |
| 5,501,727 A | 3/1996 | Wang et al. | |
| 5,530,038 A | 6/1996 | Yamamoto et al. | |
| 5,545,676 A | 8/1996 | Palazzotto et al. | |
| 5,607,663 A | 3/1997 | Rozzi et al. | |
| 5,662,887 A | 9/1997 | Rozzi et al. | |

(Continued)

FOREIGN PATENT DOCUMENTS

| | | |
|---|---|---|
| EP | 0 237 233 | 9/1987 |
| EP | 0 373 384 | 6/1990 |
| EP | 0 375 160 | 6/1990 |
| EP | 0 661 034 | 7/1995 |

(Continued)

OTHER PUBLICATIONS

Connors, K. A., "Chemical Kinetics, The Study of Reaction Rates in Solution", *VCH*, 1990, Chapter 2.

Rodrigues et al., "Cationic Photopolymerization Of Tetrahydrofuran: A Mechanistic Study On The Use Of A Sulfonium Salt-Phenothiazine Inititaion System", *Journal of Polymer Science: Part A: Polymer Chemistry*, vol. 39, pp. 46-55, 2001.

Gomurashvili et al., "Phenothiazine Photosensitizers For Onium Salt Photoinitiated Cationic Polymerization", *Journal of Polymer Science: Part A: Polymer Chemistry*, vol. 39, pp. 1187-1197, 2001.

(Continued)

*Primary Examiner*—Susan Berman
(74) *Attorney, Agent, or Firm*—Jean A. Lown

(57) ABSTRACT

Compositions are provided that include a photoinitiator system for free radical polymerization reactions. More specifically, the photoinitiator includes an arylsulfinate ion and a triarylsulfonium ion. Polymerization methods are also provided those include the photoinitiator in a photopolymerizable composition. Additionally, triarylsulfonium arylsulfinate salts are disclosed.

20 Claims, No Drawings

U.S. PATENT DOCUMENTS

| | | |
|---|---|---|
| 5,866,630 A | 2/1999 | Mitra et al. |
| 5,876,208 A | 3/1999 | Mitra et al. |
| 5,888,491 A | 3/1999 | Mitra et al. |
| 5,998,495 A | 12/1999 | Oxman et al. |
| 6,017,660 A | 1/2000 | Palazzotto et al. |
| 6,030,606 A | 2/2000 | Holmes |
| 6,187,833 B1 | 2/2001 | Oxman et al. |
| 6,204,302 B1 | 3/2001 | Rawls et al. |
| 6,312,668 B2 | 11/2001 | Mitra et al. |
| 6,331,080 B1 | 12/2001 | Cole et al. |
| 6,387,981 B1 | 5/2002 | Zhang et al. |
| 6,444,725 B1 | 9/2002 | Trom et al. |
| 6,458,868 B1 | 10/2002 | Okada et al. |
| 6,528,555 B1 | 3/2003 | Nikutowski et al. |
| 6,566,413 B1 | 5/2003 | Weinmann et al. |
| 6,572,693 B1 | 6/2003 | Wu et al. |
| 6,624,236 B1 | 9/2003 | Bissinger et al. |
| 6,759,177 B2 | 7/2004 | Shimada et al. |
| 6,777,460 B2 | 8/2004 | Palazzotto et al. |
| 7,026,367 B2 * | 4/2006 | Kalgutkar ............... 522/31 |
| 7,030,169 B2 * | 4/2006 | Kalgutkar et al. ........... 522/31 |
| 7,064,152 B2 * | 6/2006 | Kalgutkar et al. ........... 522/15 |
| 2003/0054288 A1 | 3/2003 | Shimada et al. |
| 2003/0166816 A1 | 9/2003 | Bissinger et al. |

FOREIGN PATENT DOCUMENTS

| | | |
|---|---|---|
| EP | 0 712 622 | 5/1996 |
| EP | 1 051 961 | 11/2000 |
| EP | 1 269 967 | 1/2003 |
| JP | 2002-341519 | * 11/2002 |
| WO | WO 00/38619 | 7/2000 |
| WO | WO 00/42092 | 7/2000 |
| WO | WO 01/07444 | 2/2001 |
| WO | WO 01/30306 | 5/2001 |
| WO | WO 01/30307 | 5/2001 |
| WO | WO 01/92271 | 12/2001 |
| WO | WO 02/092021 | 11/2002 |

OTHER PUBLICATIONS

Crivello et al., "Dye-Sensitized Photoinitiated Cationic Polymerization. The System: Perylene-Triarylsulfonium Salts", *General Electric Corporate Research and Development*, Schenectady, NY, pp. 1059-1065.

"Pigments-Inorganic" and "Pigments-Organic", *Kirk-Othmer Encyclopedia of Chemical Technology*, Third ed., vol. 17, pp. 788-871, John Wiley & Sons, NY, 1982.

Pearson, "Photoconductive Polymers", *Pure and Appl. Chem.*, 49, pp. 463-477, 1977.

Beringer et al., "Diaryliodonium Salts. IX. The Synthesis of Substituted Diphenyliodonium Salts", *Am. Chem. Soc.*, 81, 342-351 (1959).

Dorman et al., "Carbon-13 Nuclear Magnetic Resonance Spectroscopy. Quantitative Correlations of the Carbon Chemical Shifts of Acyclic Alkenes", *J. Org. Chem.*, 36, 2757-2766 (1971).

Sims et al., "Studies on the Mechanism by Which Cyanine Dyes Measure Membrane Potential in Red Blood Cells and Phosphatidylcholine Vesicles", *Biochemistry*, vol. 13, No. 16, 3315-3330 (1974).

Safran et al., "Phase Diagrams for Microemulsions", *Phys.Rev.Lett.*, vol. 50, No. 24, pp. 1930-1933 (1983).

Buonocore et al., "A Report on A Resin Composition Capable Of Bonding To Human Dentin Surfaces", *J.Dent.Res.*, vol. 35, No. 6, pp. 846-851 (1956).

Leung et al., "Microemulsions: Formation, Structure, Properties, and Novel Applications", *Surfactants in Chemical/Process Engineering*, Marcel Dekker, Inc. NY, vol. 28, Chapter 9, pp. 315-367 (1988).

Ostrovsky et al., "Mechanism of Microemulsion Formation In Systems With Low Interfacial Tension: Occurrence, Properties, and Behavior of Microemulsions", *J.Colloid.Interface.Sci.*, vol. 102, No. 1, pp. 206-226 (1984).

* cited by examiner

PHOTOINIATORS HAVING TRIARYLSULFONIUM AND ARYLSULFINATE IONS

STATEMENT OF PRIORITY

This application is a continuation of application Ser. No. 10/672,554 filed on Sep. 26, 2003 now U.S. Pat. No. 7,026,367, incorporated herein by reference.

TECHNICAL FIELD

Photoinitiators for free radical polymerization reactions are provided that include triarylsulfonium ions and arylsulfinate ions.

BACKGROUND

Free radical polymerization reactions can be photoinitiated. The photoinitiator system can be based on various chemical approaches. For example, free radical polymerization reactions can be photoinitiated using a three-component photoinitiator system that includes an electron acceptor, an electron donor, and a sensitizing compound. The sensitizing compound usually absorbs actinic radiation resulting in the formation of an excited sensitizing compound. The electron donor can donate an electron to the excited sensitizing compound. That is, the sensitizing compound is reduced and the electron donor is oxidized. The reduced sensitizing compound is a radical anion that can donate an electron to an electron acceptor to yield an initiating free radical for the polymerization reaction. The initiating free radical is the reduced electron acceptor. In some instances of a three-component photoinitiator system, the oxidized electron donor is a radical species that also can function as an initiating free radical.

Other photoinitiator systems include a sensitizing compound and an electron donor but no electron acceptor. The sensitizing compound is usually an organic dye, an organic pigment, or an inorganic pigment. The sensitizing compound can absorb actinic radiation to form an exited sensitizing compound. The electron donor typically donates an electron to the excited sensitizing compound resulting in the oxidation of the electron donor. The oxidized electron donor is a radical species that functions as an initiating free radical for polymerization reactions.

In other free radical photopolymerization reactions, a salt such as a triarylsulfonium salt can generate an initiating free radical. Triarylsulfonium salts typically absorb ultraviolet radiation to form an excited triarylsulfonium ion. The excited triarylsulfonium ion can then photodegrade, abstract a hydrogen atom from another species present in the composition, and ultimately form a radical that can function as an initiating free radical for a polymerization reaction.

SUMMARY

Compositions are provided that include a photoinitiator system for free radical polymerization reactions. More specifically, the photoinitiator includes an arylsulfinate ion and a triarylsulfonium ion. Polymerization methods are also provided that include the photoinitiator in a photopolymerizable composition. Additionally, triarylsulfonium arylsulfinate salts are disclosed.

One aspect of the invention provides a composition that includes an arylsulfinate salt and a triarylsulfonium salt. The arylsulfinate salt has an anion of Formula I $$Ar^1\text{—}SO_2^- \qquad \qquad I$$

and a cation having at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. 

A second aspect of the invention provides a composition that includes an ethylenically unsaturated monomer and a triarylsulfonium arylsulfinate salt. The triarylsulfonium arylsulfinate salt has an anion of Formula I $$Ar^1\text{—}SO_2^- \qquad \qquad I$$

where $Ar^1$ is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group.

A third aspect of the invention provides a method of photopolymerization that includes irradiating a photopolymerizable composition with actinic radiation until the photopolymerizable composition gels or hardens. The photopolymerizable composition includes ethylenically unsaturated monomers, an arylsulfinate salt, and a triarylsulfonium salt.

A fourth aspect of the invention provides a method of photopolymerization that includes irradiating a photopolymerizable composition with actinic radiation until the photopolymerizable composition gels or hardens. The photopolymerizable composition includes ethylenically unsaturated monomers and a triarylsulfonium arylsulfinate salt.

A fifth aspect of the invention provides a triarylsulfonium arylsulfinate salt.

The above summary is not intended to describe each disclosed embodiment or every implementation of the present invention. The detailed description section that follows more particularly exemplifies these embodiments.

DETAILED DESCRIPTION OF PREFERRED EMBODIMENTS

Compositions are provided that include a photoinitiator system for free radical polymerization reactions. More specifically, the photoinitiator includes an arylsulfinate ion and a triarylsulfonium ion. Polymerization methods are also provided for preparing a polymeric material using a free radical polymerization reaction. The polymerization reaction is photoinitiated. Additionally, triarylsulfonium arylsulfinate salts are disclosed.

Definitions

As used herein, the terms "a", "an", and "the" are used interchangeably with "at least one" to mean one or more of the elements being described.

As used herein, the term "acyl" refers to a monovalent group of formula —(CO)$R^a$ where $R^a$ is an alkyl or aryl group.

As used herein, the term "actinic radiation" refers to electromagnetic radiation capable of producing photochemical activity.

As used herein, the term "alkenyl" refers to a monovalent radical of an alkene (i.e., an alkene is an aliphatic compound having at least one carbon-carbon double bond).

As used herein, the term "alkoxy" refers to a group of monovalent formula —OR where R is an alkyl group.

As used herein, the term "alkoxycarbonyl" refers to a monovalent group of formula —(CO)OR where R is an alkyl group.

As used herein, the term "alkoxycarbonyloxy" refers to a monovalent group of formula —O(CO)OR where R is an alkyl group.

As used herein, the term "alkoxysulfonyl" refers to a monovalent group having the formula —SO$_3$R where R is an alkyl group.

As used herein, the term "alkyl" refers to a monovalent radical of an alkane. The alkyl can be linear, branched, cyclic, or combinations thereof and typically contains 1 to 30 carbon atoms. In some embodiments, the alkyl group contains 1 to 20, 1 to 14, 1 to 10, 4 to 10, 4 to 8, or 1 to 4 carbon atoms. Examples of alkyl groups include, but are not limited to, methyl, ethyl, n-propyl, isopropyl, n-butyl, isobutyl, tert-butyl, n-octyl, n-heptyl, n-hexyl, cyclohexyl, ethylhexyl, and the like.

As used herein, the term "alkylcarbonylamido" refers to a monovalent group of formula —NR$^b$(CO)R where R is an alkyl and R$^b$ is a hydrogen, alkyl, or aryl group.

As used herein, the term "alkylcarbonyloxy" refers to a monovalent group of formula —O(CO)R where R is an alkyl.

As used herein, the term "alkylsulfonamido" refers to a monovalent group of formula —NR$^b$SO$_2$R where R is an alkyl and R$^b$ is a hydrogen, alkyl, or aryl group.

As used herein, the term "alkynyl" refers to a monovalent radical of an alkyne (i.e., an alkyne is an aliphatic compound having at least one carbon-carbon triple bond).

As used herein, the term "alkylsulfonyl" refers to a monovalent group of formula —SO$_2$R where R is an alkyl group.

As used herein, the term "alkylthio" refers to a monovalent group of formula —SR where S is sulfur and R is an alkyl.

As used herein, the term "amino" refers to a monovalent group of formula —N(R$^b$)$_2$ where each R$^b$ is independently hydrogen, alkyl, or aryl group. In a primary amino group, each R$^b$ group is hydrogen. In a secondary amino group, one of the R$^b$ groups is hydrogen and the other R$^b$ group is either an alkyl or aryl. In a tertiary amino group, both of the R$^b$ groups are an alkyl or aryl.

As used herein, the term "aminocarbonyl" refers to a monovalent group of formula —(CO)N(R$^b$)$_2$ where each R$^b$ is independently hydrogen, alkyl, or aryl.

As used herein, the term "aralkyl" refers to a monovalent group of formula —RAr where Ar is an aryl group and R is an alkylene.

As used herein, the term "aromatic" refers to both carbocyclic aromatic compounds or groups and heteroaromatic compounds or groups. A carbocyclic aromatic compound is a compound that contains only carbon atoms in an aromatic ring structure. A heteroaromatic compound is a compound that contains at least one heteroatom selected from S, O, N, or combinations thereof in an aromatic ring structure.

As used herein, the term "aryl" refers to a monovalent aromatic carbocyclic radical. The aryl can have one aromatic ring or can include up to 5 ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "arylcarbonylamido" refers to a monovalent group of formula —NR$^b$(CO)Ar where R$^b$ is hydrogen, alkyl, or aryl and Ar is an aryl.

As used herein, the term "arylcarbonyloxy refers to a monovalent group of formula —O(CO)Ar where Ar is an aryl group.

As used herein, the term "aryloxy" refers to a monovalent group of formula —OAr where Ar is an aryl group.

As used herein, the term "aryloxycarbonyl" refers to a monovalent group of formula —(CO)OAr where Ar is an aryl group.

As used herein, the term "aryloxycarbonyloxy" refers to a monovalent group of formula —O(CO)OAr where Ar is an aryl group.

As used herein, the term "aryloxysulfonyl" refers to a monovalent group having the formula —SO$_3$Ar where Ar is an aryl group.

As used herein, the term "arylsulfonyl" refers to a monovalent group having the formula —SO$_2$Ar where Ar is an aryl group.

As used herein, the term "arylthio" refers to a monovalent group having the formula —SAr where Ar is an aryl group.

As used herein, the term "azo" refers to a divalent group of formula —N=N—.

As used herein, the term "boryl" refers to a monovalent group of formula —B(Ar)$_2$ where B is boron and Ar is an aryl group.

As used herein, the term "carbonyl" refers to a divalent group of formula —(CO)— where the carbon atom is connected to the oxygen atom by a double bond.

As used herein, the term "carboxy" refers to a monovalent group of formula —COOH.

As used herein, the term "conjugated" refers to unsaturated compounds having at least two carbon-carbon double or triple bonds with alternating carbon-carbon single bonds and carbon-carbon double or triple bonds.

As used herein, the term "cyano" refers to a monovalent group of formula —CN.

As used herein, the term "dialkylphosphonato" refers to a monovalent group of formula —(PO)(OR)$_2$ where R is an alkyl. As used herein the formula "(PO)" indicates that the phosphorus atom is attached to an oxygen atom with a double bond.

As used herein, the term "diarylphosphonato" refers to a monovalent group of formula —(PO)(OAr)$_2$ where Ar is a aryl.

As used herein, the term "diarylstibino" refers to a monovalent group of formula —Sb(Ar)$_2$ where Ar is an aryl group.

As used herein, the term "diarylarsino" refers to a monovalent group of formula —As(Ar)$_2$ where Ar is an aryl group.

As used herein, the term "electron donating" refers to a substituent that can donate electrons. Suitable examples include, but are not limited to, a primary amino, secondary amino, tertiary amino, hydroxy, alkoxy, aryloxy, alkyl, or combinations thereof.

As used herein, the term "electron withdrawing" refers to a substituent that can withdraw electrons. Suitable examples include, but are not limited to, a halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, azo, alkenyl, alkynyl, dialkylphosphonato, diarylphosphonato, aminocarbonyl, or combinations thereof.

As used herein, the term "fluoroalkyl" refers to an alkyl group that has at least one hydrogen atom replaced with a fluorine atom.

As used herein, the term "formyl" refers to a monovalent group of formula —(CO)H where the carbon is attached to the oxygen atom with a double bond.

As used herein, the term "halo" refers to a halogen group (i.e., F, Cl, Br, or I). In some embodiments, the halo group is F or Cl.

As used herein, the term "halocarbonyl" refers to a monovalent group of formula —(CO)X where X is a halogen group (i.e., F, Cl, Br, or I).

As used herein, the term "heteroaryl" refers to a monovalent radical of a five to seven member aromatic ring that includes one or more heteroatoms independently selected from S, O, N, or combinations thereof in the ring. Such a heteroaryl ring can be connected to or fused to up to five ring structures that are aromatic, aliphatic, or combinations thereof. Examples of heteroaryl groups include, but are not limited to, quinolinyl, isoquinolinyl, quinazolinyl, quinoxalinyl, cinnolinyl, benzofuranyl, benzomercaptophenyl, benzoxazolyl, benzothiazolyl, benzimidazolyl, indolyl, phthalazinyl, benzothiadiazolyl, benzotriazinyl, phenazinyl, phenanthridinyl, acridinyl, and indazolyl, and the like.

As used herein, the term "heterocyclic" refers to a monovalent radical having a ring structure that is saturated or unsaturated and that includes one or more heteroatoms independently selected from S, O, N, or combinations thereof in the ring. The heterocyclic group can be a single ring, bicyclic, or can be fused to another cyclic or bicyclic group. The fused cyclic or bicyclic group can be saturated or unsaturated and can be carbocyclic or contain heteroatoms.

As used herein, the term "hydroxy" refers to a monovalent group of formula —OH.

As used herein, the term "imino" refers to a divalent group of formula —N($R^b$)— where $R^b$ is hydrogen, alkyl, or aryl.

As used herein, the term "mercapto" refers to a monovalent group of formula —SH.

As used herein, the term "methylene" refers to a divalent group of formula —C($R^b$)$_2$— where each $R^b$ is independently a hydrogen, alkyl, or aryl.

As used herein, the term "N-alkylaminocarbonyl" refers to a monovalent group of formula —(CO)NR$^d$R where R$^d$ is an alkyl or hydrogen and R is an alkyl.

As used herein, the term "N-alkylsulfamyl" refers to a monovalent group of formula —SO$_2$NR$^d$R where R$^d$ is an alkyl or hydrogen and R is an alkyl.

As used herein, the term "N-arylaminocarbonyl" refers to a monovalent group of formula —(CO)NR$^c$Ar where R$^c$ is an aryl or hydrogen and Ar is an aryl.

As used herein, the term "N-arylsulfamyl" refers to a monovalent group of formula —SO$_2$NR$^c$Ar where R$^c$ is an alkyl or hydrogen and Ar is aryl.

As used herein, the term "oxo" refers to a divalent group of formula —O—.

As used herein, the term "perfluoroalkyl" refers to an alkyl group that has all the hydrogen atoms replaced with fluorine atoms. A perfluoroalkyl is a subset of a fluoroalkyl.

As used herein, the term "perfluoroalkylsulfonyl" refers to a group of formula —SO$_2$R$_f$ where R$_f$ is a perfluoroalkyl.

As used herein, the term "polymerization" refers to forming a higher weight material from monomer or oligomers. The polymerization reaction also can involve a cross-linking reaction.

As used herein when referring to a composition containing an initiator system and photopolymerizable material, the term "stable" means that the composition can be stored for at least one day without any visible gel formation at room temperature.

As used herein when referring to a compound, the term "stability" refers to the length of time needed to oxidize 50 weight percent of the compound ($t_{1/2}$) at room temperature (i.e., 20° C. to 25° C.) which can be calculated using pseudo-first order kinetics as described in K. A. Connors, Chemical Kinetics: The Study of Reaction Rates in Solution, Chapter 2, VCH, New York, 1990.

As used herein, the term "sulfinyl" refers to a divalent group having the formula —(SO)—.

As used herein, the term "sulfonyl" refers to a divalent group having the formula —SO$_2$—.

As used herein, the term "sulfo" refers to a monovalent group having the formula —SO$_3$H.

As used herein, the term "thio" refers to a divalent group of formula —S—.

As used herein, the term "trialkylgermano" refers to a group having the formula —Ge(Ar)$_2$ where Ar is an aryl group.

As used herein, the term "trialkylsiloxy" refers to a monovalent group of formula —OSiR$_3$ where R is an alkyl.

Composition

Triarylsulfonium salts, in the absence of a sensitizing compound, typically cannot generate an initiating free radical for polymerization reactions when exposed to visible radiation. A photoinitiator system that can be activated using visible radiation is desirable for some applications. Visible light sources are typically less expensive and less hazardous than ultraviolet light sources. Additionally, compared to ultraviolet radiation, visible radiation can typically transmit more readily through various substrates such as polymeric materials.

One aspect of the invention provides compositions that include an arylsulfinate salt and a triarylsulfonium salt. The compositions can function as a photoinitiator system for free radical polymerization reactions. Although not intending to be bound by theory, it is believed that the arylsulfinate salt can absorb actinic radiation to form an excited arylsulfinate salt. The excited arylsulfinate salt can transfer an electron to the triarylsulfonium salt resulting in the formation of an arylsulfinate radical. The arylsulfinate radical can initiate free radical polymerization reactions. In some instances, the reduced triarylsulfonium salt can photodegrade to produce other initiating free radicals.

One component of the composition is an arylsulfinate salt. The arylsulfinate salt has an anion of Formula I

     I and a cation that contains at least one carbon atom and either a positively charged nitrogen atom or a positively charged phosphorus atom. The Ar$^1$ group in Formula I is a substituted phenyl, an unsubstituted or substituted C$_{7-30}$ aryl, or an unsubstituted or substituted C$_{3-30}$ heteroaryl. A substituted Ar$^1$ group can have a substituent that is an electron withdrawing group or an electron withdrawing group in combination with an electron donating group.

The arylsulfinate salt is typically soluble in monomers capable of undergoing free radical polymerization reactions and in a variety of non-polar and polar solvents. As used herein, the term "soluble" refers to a compound that can be dissolved in an amount at least equal to 0.05 moles/liter, at least equal to 0.07 moles/liter, at least equal to 0.08 moles/liter, at least equal to 0.09 moles/liter, or at least equal to 0.1 moles/liter in a given material such as a solvent or monomer.

In some arylsulfinate salts, the Ar$^1$ group is a substituted phenyl or an unsubstituted or substituted C$_{7-30}$ aryl group having a carbocyclic aromatic ring. The aryl group can have a single carbocyclic aromatic ring or can have additional carbocyclic rings that are fused or connected to a carbocyclic aromatic ring. Any fused or connected rings can be saturated or unsaturated. The aryl often contains up to 5 rings, up to 4 rings, up to 3 rings, up to 2 rings, or one ring. The aryl group usually has up to 30 carbon atoms, up to 24 carbon atoms, up to 18 carbon atoms, up to 12 carbon atoms, or 6 carbon atoms. Examples of aryl groups having a single ring or multiple fused rings include, but are not limited to, phenyl, anthryl, naphthyl, acenaphthyl, phenanthryl, phenanthrenyl, perylenyl, and anthracenyl. A single bond, methylene group (i.e., —C($R^b$)$_2$— where each $R^b$ is independently hydrogen, alkyl, or aryl), carbonyl group (i.e., —(CO)—), or combinations thereof can connect multiple rings. Examples of aryl groups having multiple connected rings include, but are not limited to, anthraquinonyl, anthronyl, biphenyl, terphenyl, 9,10-dihydroanthracenyl, and fluorenyl.

In other arylsulfinate salts, the $Ar^1$ group in Formula I can be an unsubstituted or substituted heteroaryl that has a five to seven member aromatic ring that includes one or more heteroatoms independently selected from S, O, N, or combinations thereof in the ring. The heteroaryl can have a single ring or can have multiple rings connected or fused together. Any additional connected or fused rings can be carbocyclic or contain a heteroatom and can be saturated or unsaturated. The heteroaryl group often has up to 5 rings, up to 4 rings, up to 3 rings, up to 2 rings, or one ring. The heteroaryl typically contains up to 30 carbon atoms. In some embodiments, the heteroaryl contains up to 20 carbon atoms, up to 10 carbon atoms, or up to 5 carbon atoms. Examples of heteroaryl groups include, but are not limited to, quinolinyl, isoquinolinyl, quinazolinyl, quinoxalinyl, cinnolinyl, benzofuranyl, benzomercaptophenyl, benzoxazolyl, benzothiazolyl, benzimidazolyl, indolyl, phthalazinyl, benzothiadiazolyl, benzotriazinyl, phenazinyl, phenanthridinyl, acridinyl, azaphenanthrenyl, and indazolyl.

The $Ar^1$ group in Formula I, in some embodiments, can be unsubstituted with an electron withdrawing group or an electron withdrawing group in combination with an electron donating group. Electron donating groups can be selected, for example, from a primary amino, secondary amino, tertiary amino, hydroxy, alkoxy, aryloxy, alkyl, or combinations thereof. Electron withdrawing groups can be selected, for example, from a halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

In some embodiments, the $Ar^1$ group includes an electron withdrawing group that is conjugated to the sulfinate group. For example, the $Ar^1$ group can be a phenyl substituted with an electron withdrawing group selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof. In some arylsulfinate anions, the electron withdrawing group is selected from cyano, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof. In other arylsulfinate anions, the electron withdrawing group is a halo group. In still other the $Ar^1$ group substituents include an electron withdrawing group in addition to an electron donating group. For example, the $Ar^1$ group substituents can include an alkyl and an electron withdrawing group.

Specific examples of the arylsulfinate anion of Formula I include, but are not limited to, 4-chlorobenzenesulfinate, 4-cyanobenzenesulfinate, 4-ethoxycarbonylbenzenesulfinate, trifluoromethylbenzenesulfinate, 3-trifluoromethylbenzenesulfinate, 1-naphthalenesulfinate, 2-naphthalenesulfinate, and 1-anthraquinonesulfinate.

The arylsulfinate salts have a cation with at least one carbon atom and either a positively charged nitrogen atom or a positively charged phosphorus atom. In some embodiments, the cation of the arylsulfinate salt is of Formula II

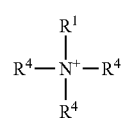

where $R^1$ is an alkyl or aryl and each $R^4$ is independently hydrogen, alkyl, or aryl. The $R^1$ and $R^4$ groups can be unsubstituted or substituted. An alkyl group can be substituted with a hydroxy. An aryl can be substituted with an alkyl, hydroxy, or combinations thereof.

In some examples of Formula II, $R^1$ and each $R^4$ group are independently a $C_{2-30}$ alkyl that is unsubstituted or substituted with a hydroxy. For example, $R^1$ and each $R^4$ independently can be an alkyl group having up to 20, up to 10, up to 8, up to 6, or up to 4 carbon atoms. The alkyl group often has at least 2, at least 3, at least 4, at least 6, or at least 8 carbon atoms. The alkyl group can have 4 to 30, 8 to 30, 3 to 10, 4 to 10, 4 to 8, or 4 to 6 carbon atoms in some compounds. In a specific example, the cation of the arylsulfinate salt is a tetrabutylammonium ion.

In other examples of Formula II, $R^1$ and two $R^4$ groups are each independently a $C_{2-30}$ alkyl that can be unsubstituted or substituted with a hydroxy. The remaining $R^4$ group is hydrogen. In still other examples, $R^1$ and one $R^4$ group are each independently a $C_{4-30}$ alkyl that is unsubstituted or substituted with a hydroxy; and the two remaining $R^4$ groups are hydrogen. In yet other examples, $R^1$ is a $C_{8-30}$ alkyl that is unsubstituted or substituted with a hydroxy; and the $R^4$ groups are hydrogen.

The $R^1$ group and each of the $R^4$ groups in Formula II independently can be an aryl group that is unsubstituted or substituted with an alkyl or hydroxy. An exemplary cation is tetraphenylammonium ion. In another example, $R^1$ and one $R^4$ independently are an aryl group that is unsubstituted or substituted with an alkyl or hydroxy; and the two remaining $R^4$ groups are hydrogen. An exemplary cation is diphenylammonium ion.

In other embodiments, the cation of the arylsulfinate salt is a ring structure that includes a four to twelve member heterocyclic group with a positively charged nitrogen atom. The heterocyclic group can be saturated or unsaturated and can contain up to three heteroatoms selected from nitrogen, oxygen, sulfur, or combinations thereof (i.e., there is one positively charged nitrogen atom and up to two other heteroatoms selected from nitrogen, oxygen, sulfur, or combinations thereof). The ring structure can be unsubstituted or have a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof.

The heterocyclic group in the cationic ring structure can be a single ring, bicyclic, or can be fused to another cyclic or bicyclic group. The fused cyclic or bicyclic group can be saturated or unsaturated and can have 0 to 3 heteroatoms. The ring structure can include up to 30 carbon atoms, up to 24 carbon atoms, up to 18 carbon atoms, up to 12 carbon atoms, up to 6 carbon atoms, or up to 4 carbon atoms and up to 6 heteroatoms, up to 4 heteroatoms, up to 2 heteroatoms, or 1 heteroatom. In some embodiments, the ring structure is a 4 to 12 member heterocyclic group that is a fused to an aromatic ring having 0 to 3 heteroatoms.

Suitable examples of five member heterocyclic groups that contain a positively charged nitrogen atom include, but are not limited to, a pyrrolium ion, pyrazolium ion, pyrrolidinium ion, imidazolium ion, triazolium ion, isoxazolium ion, oxazolium ion, thiazolium ion, isothiazolium ion, oxadiazolium ion, oxatriazolium ion, dioxazolium ion, and oxathiazolium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof. In some applications, the cation is an imidazolium ion or oxazolium ion that is unsubstituted or substituted.

The five member heterocyclic groups can be fused to another cyclic group. In some exemplary ring structures, a five membered heterocyclic group is fused to an aromatic group. Exemplary ring structures include, but are not limited to, an indole ion, indazolium ion, benzopyrrolidinium ion, benzimidazolium ion, benzotriazolium ion, benzisoxazolium ion, benzoxazolium ion, benzothiazolium ion, benzisothiazolium ion, benzoxadiazolium ion, benzoxatriazolium ion, benzodioxazolium ion, benzoxathiazolium ion, carbozolium ion, and purinium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof. In some applications, the cation is a benzoxazolium ion or a benzothiazolium ion that is unsubstituted or substituted.

Suitable examples of six member heterocyclic groups that contain a positively charged nitrogen atom include, but are not limited to, a pyridinium ion, pyridazinium ion, pyrimidinium ion, pyrazinium ion, piperazinium ion, triazinium ion, oxazinium ion, piperidinium ion, oxathiazinium ion, oxadiazinium ion, and morpholinium ion. These ions can be unsubstituted or substituted with an alkyl, aryl, acyl, alkoxy, aryloxy, halo, mercapto, amino, hydroxy, azo, cyano, or carboxy, alkoxycarbonyl, aryloxycarbonyl, halocarbonyl, or combinations thereof. In some applications, the cation is a pyridinium ion or a morpholinium ion that is unsubstituted or substituted.

The six member heterocyclic groups can be fused to another cyclic group. In some exemplary ring structures, a six membered heterocyclic group is fused to an aromatic group. Exemplary ring structures include, but are not limited to, isoquinolinium ion, quinolinium ion, cinnolinium ion, quinazolinium ion, benzopyrazinium ion, benzoperazinium ion, benzotriazinium ion, benzoxazinium ion, benzopiperidinium ion, benzoxathiazinium ion, benzoxadizinium ion, benzomorpholinium ion, naphtyridinium ion, and acridinium ion. These ions can be unsubstituted or substituted with an alkyl, aryl, acyl, alkoxy, aryloxy, halo, mercapto, amino, hydroxy, azo, cyano, or carboxy, alkoxycarbonyl, aryloxycarbonyl, halocarbonyl, or combinations thereof.

Suitable examples of seven member heterocyclic groups that contain a positively charged nitrogen atom include, for example, an azepinium ion and diazepinium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof.

Examples of heterocyclic groups that are bicyclic include, but are not limited to, N-alkylated or N-protonated 1,4-diazabicyclo [2.2.2] octane and N-alkylated or N-protonated 1-azabicyclic[2.2.2] octane that is unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof.

In other embodiments, the cation of the arylsulfinate salt contains a positively charged phosphorus atom of Formula III

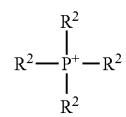

III where each $R^2$ is independently an alkyl or aryl that is unsubstituted or substituted. An alkyl group can be substituted with a hydroxy. An aryl can be substituted with an alkyl, hydroxy, or combinations thereof.

In some examples of Formula III, all of the $R^2$ groups are aryl groups. For example, the cation is a tetraphenylphosphonium ion. In other examples, one, two, or three of the $R^2$ groups are an aryl with the remaining $R^2$ group or groups being a $C_{2-30}$ alkyl.

Some of the arylsulfinate salts can have an anion of Formula IV

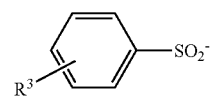

IV and a cation that includes a positively charged nitrogen atom. In Formula IV, $R^3$ can be in an ortho, para, or meta position of the benzene ring and is an electron withdrawing group selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, or aminocarbonyl. In some compounds, $R^3$ is selected from cyano, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, or aminocarbonyl. In other compounds, $R^3$ is a halo, cyano, or alkoxycarbonyl group.

Specific examples Formula IV where $R^3$ is located in the para position of the phenyl ring include 4-cyanobenzenesulfinate, 4-chlorobenzenesulfinate, 4-ethoxycarbonylbenzenesulfinate, and 4-trifluoromethylbenzenesulfinate. A specific example of $R^3$ located in the meta position of the phenyl ring includes 3-trifluoromethylbenzenesulfinate.

For some applications, the arylsulfinate salt includes an anion of Formula IV and a cation that is a tetraalkylammonium ion. The alkyl groups of the tetraalkylammonium ion can be the same or different and typically contain 2 to 30 carbon atoms. For example, the alkyl groups can contain 4 to 30 carbon atoms, 8 to 30 carbon atoms, 3 to 10 carbon atoms, 4 to 10 carbon atoms, 4 to 8 carbon atoms, or 4 to 6 carbon atoms. Specific arylsulfinate salts include, but are not limited to, tetrabutylammonium 4-chlorobenzenesulfinate, tetrabutylammonium 4-cyanobenzenesulfinate, tetrabutylammonium 4-ethoxycarbonylbenzenesulfinate, tetrabutylammonium 4-trifluoromethylbenzenesulfinate, and tetrabutylammonium 3-trifluoromethylbenzenesulfinate.

Other specific examples of arylsulfinate salts include, but are not limited to, tetrabutylammonium 1-naphthalenesulfinate, tetrabutylammonium 2-naphthalenesulfinate, tetrabutylammonium 1-anthraquinonesulfinate, 1-ethyl-3-methylimidazolium 4-cyanobenzenesulfinate, N,N-morpholinium 4-cyanobenzenesulfinate, 3-ethyl-2-methylbenxoxazolium 4-cyanobenzenesulfinate, 1-methyl-4-aza-1-azoniabicyclo [2.2.2]octane 4-cyanobenzenesulfinate, and N-hexadecylpyridinium 4-cyanobenzenesulfinate.

In some embodiments, the arylsulfinate salts are colored and absorb visible radiation. For example, the arylsulfinate salts can have a yellow color. Examples of colored arylsulfinate salts include, but are not limited to, those having a cation that is benzenesulfinate substituted with an electron withdrawing group selected from cyano, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof. Other colored arylsulfinate salts include those having a cation with multiple fused rings such as, for example, 1-naphthalenesulfinate, 2-naphthalenesulfinate, and 1-anthroquinonesulfinate.

Some arylsulfinate salts have an oxidation potential in N,N-dimethylformamide of 0.0 to +0.4 volts, +0.08 to +0.4 volts, +0.08 to +0.3 volts, or +0.08 to +0.3 volts versus a silver/silver nitrate reference electrode. The oxidation potential can be determined using cyclic voltammetry. The compound of interest is typically dissolved in a non-aqueous solvent (i.e., N,N-dimethylformamide) containing a supporting electrolyte (i.e., 0.1 moles/liter tetrabutylammonium hexafluorophosphate). The resulting solution is purged with an inert gas such as argon. A three-electrode configuration is used that includes a working electrode (i.e., a glassy carbon electrode), a reference electrode (i.e., a silver wire in a 0.01 moles/liter solution of silver nitrate dissolved in acetonitrile), and a counter electrode (i.e., a platinum wire). The oxidation potential is the voltage corresponding to the maximum current for the oxidation reaction.

Another component of the composition is a triarylsulfonium salt. The triarylsulfonium ion typically is of Formula V

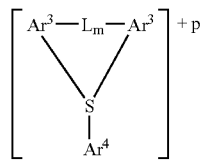

where each $Ar^3$ and $Ar^4$ are independently a $C_{6-30}$ aryl or a $C_{3-30}$ heteroaryl that is unsubstituted or substituted; L is a divalent linking group selected from a single bond, oxo, thio, sulfinyl, carbonyl, sulfonyl, methylene, or imino; p is an integer equal to or greater than 1; and m is an integer equal to 0 or 1. The arylsulfonium ions can be substituted with up to 30 carbon atoms and up to 10 heteroatoms selected from N, S, O, P, As, Si, Sb, B, Ge, Te, or Se. In some exemplary triarylsulfonium ions, there are no substituents. In other exemplary triarylsulfonium ions, a substituent has up to 5, up to 3, or up to 1 heteroatom. The number of carbon atoms in a substituent can be, for example, up to 20, up to 10, up to 8, up to 6, up to 4, or up to 3. The charge on the cation can be altered depending on the substituents. In some embodiments, p is equal to 1 or 2.

Each $Ar^3$ and $Ar^4$ can be an aromatic group having a single or multiple rings. Examples of single ring aromatic groups include, but are not limited to, phenyl, thienyl, or furanyl. Examples of multiple ring aromatic groups include, but are not limited to, naphthyl, benzothienyl, dibenzothienyl, benzofuranyl, and dibenzofuranyl. The rings can be unsubstituted or substituted.

In some embodiments of Formula V, there is no linking group L between two of the aromatic groups (i.e., m is equal to 0). A specific example of a triarylsulfonium ion lacking a linking group is triphenylsulfonium. Specific examples of triarylsulfonium ions having a linking group (i.e., m is equal to 1) include, but are not limited to,

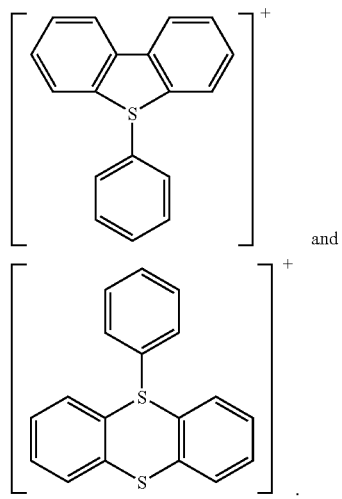

With some triarylsulfonium ions, the cations can react with each other to form cations having a higher molecular weight. For example, a triphenylsulfonium salt can include

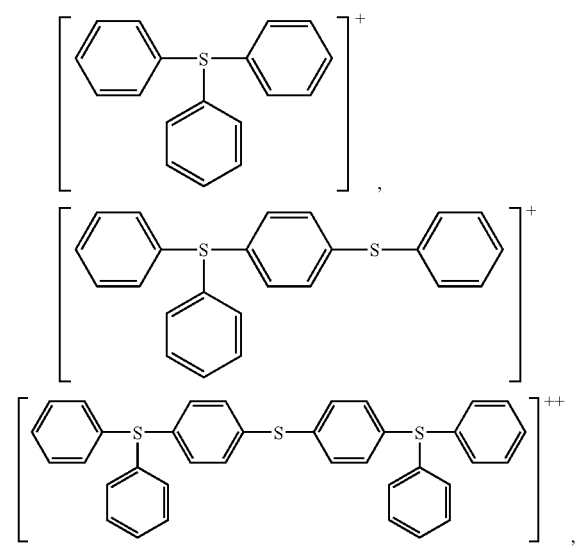

-continued

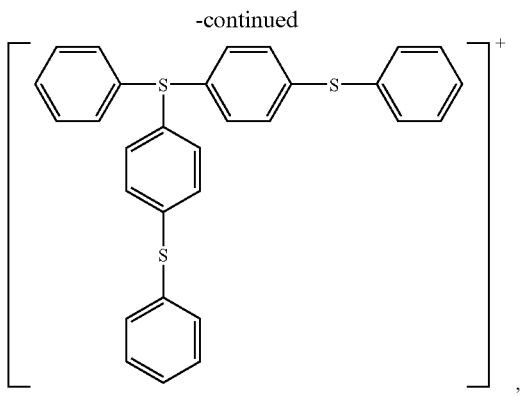

or combinations thereof. Suitable arylsulfonium salts are further described in U.S. Pat. Nos. 2,807,648, 4,069,054 and 4,216,288; and U.S. patent application Ser. No. 10/328,520, the disclosures of which are incorporated herein by reference in their entirety.

Suitable substituents for the arylsulfonium ions include, but are not limited to, alkyl (e.g., methyl, ethyl, butyl, dodecyl, and tetracosanyl); alkylcarbonyloxy (e.g., acetoxy and cyclohexanecarbonyloxy); alkynyl (e.g., ethynyl); alkoxy (e.g., methoxy, ethoxy, and butoxy); alkoxycarbonyl (e.g., methoxycarbonyl and ethoxycarbonyl); alkylthio (e.g., methylthio and ethylthio); arylthio (e.g., phenylthio); aralkyl (e.g., benzyl); alkenyl (e.g., ethenyl and allyl); aryl (e.g., cyclopentadienyl, phenyl, tolyl, naphthyl, indenyl, anthracenyl, phenanthrenyl, and perylenyl); arylcarbonyloxy (e.g., benzoyloxy); arylcarbonylamido (e.g., benzamido); aryloxy (e.g., phenoxy); aryloxycarbonyl (e.g., phenoxycarbonyl); alkoxysulfonyl (e.g., methoxysulfonyl and butoxysulfonyl); aryloxysulfonyl (e.g., phenoxysulfonyl); alkylsulfonamido (e.g., ethylsulfonamido); N-alkylaminocarbonyl (e.g., N-methylaminocarbonyl, N,N-dimethylaminocarbonyl); N-arylaminocarbonyl (e.g., N-phenylaminocarbonyl); N-alkylsulfamyl (e.g., N-methylsulfamyl); N-arylsulfamyl (e.g., N-phenylsulfamyl); alkylsulfonyl (e.g., methylsulfonyl); arylsulfonyl (e.g., phenylsulfonyl); perfluoroalkyl (e.g., trifluoromethyl, perfluoroethyl, and perfluorobutyl); perfluoroalkysulfonyl (e.g., trifluoromethylsulfonyl, perfluoroethylsulfonyl, and perfluorobutylsulfonyl); azo; boryl; halo (e.g., chloro, bromo, iodo, and fluoro); hydroxy; mercapto; diarylarsino (e.g., diphenylarsino); diarylstibino (e.g., diphenylstibino); trialkylgermano (e.g., trimethylgermano); trialkylsiloxy (e.g., trimethylsiloxy); of combinations thereof.

In some embodiments, the triarylsulfonium ion is unsubstituted or substituted with an acyl, alkyl, alkylthio, arylthio, alkylcarbonylamido, aryl, alkoxy, halo, aryloxy, or combinations thereof.

Specific examples of triarylsulfonium ions include triphenylsulfonium, diphenylnaphthylsulfonium, tritolysulfonium, anisyldiphenylsulfonium, 4-butoxyphenyldipenylsulfonium, 4-tert-butylphenyldiphenylsulfonium, 4-chlorophenyldiphenylsulfonium, tris(4-phenoxyphenyl) sulfonium, 4-acetonylphenyldiphenylsulfonium, tris(4-thiomethoxyphenyl)sulfonium, 4-acetamidophenyldiphenylsulfonium, and the like.

The anion of the triarylsulfonium salt is typically chosen to provide suitable solubility in various solvents such as alcohols, ethylenically unsaturated monomers, or combinations thereof. In some applications, the triarylsulfonium salt has a solubility in an alcohol or ethylenically unsaturated monomer in an amount of at least 0.05 mole/liter, at least 0.07 moles/liter, at least 0.08 moles/liter, at least 0.09 moles/liter, or at least 0.1 moles/liter. Suitable anions of the triarylsulfonium salts include, but are not limited to, $AsF_6^-$, $SbF_6^-$, $BF_4^-$, $PF_6^-$, $CF_3SO_3^-$, $HC(SO_2CF_3)_2^-$, $C(SO_2CF_3)_3^-$, $N(SO_2CF_3)_2^-$, tetraphenylborate, tetra(pentafluorophenyl)borate, tetra(3,5-bistrifluoromethylphenyl) borate, p-toluenesulfonate, and the like. In some embodiments, the anions are selected from $BF_4^-$, $PF_6^-$, $AsF_6^-$, $SbF_6^-$, or combinations thereof. In other embodiments, the anion is an arylsulfinate according to Formula I as described above.

The triarylsulfonium salts are often commercially available in the form of a solution. For example, triarylsulfonium $SbF_6^-$ is commercially available as a 50 weight percent solution in propylene carbonate from Dow Chemical Co., Midland Mich. (UVI-6974) and from Sartomer Company, Exton, Pa. (CD-1010). Triarylsulfonium $PF_6^-$ is commercially available as a 50 weight percent solution in propylene carbonate from Dow Chemical Co., Midland, Mich. (UVI-6990) and from Sartomer Company, Exton, Pa. (CD-1011).

The composition can further include monomers that are capable of being polymerized using a free-radical polymerization reaction. The monomers typically contain at least one ethylenically unsaturated double bond. The monomers, for example, can be monoacrylates, diacrylates, polyacrylates, monomethacrylates, dimethacrylates, polymethacrylates, or combinations thereof. Exemplary monomers include methyl acrylate, methyl methacrylate, ethyl acrylate, ethyl methacrylate, isopropyl acrylate, isopropyl methacrylate, n-hexyl acrylate, stearyl acrylate, allyl acrylate, glycerol acrylate, glycerol diacrylate, glycerol triacrylate, ethyleneglycol diacrylate, diethyleneglycol diacrylate, triethyleneglycol diacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexaacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethylacrylate. The monomers also can be bis-acrylates and bis-methacrylates of polyethylene glycol having an average molecular weight ($M_n$) of 200 to 500; copolymerizable mixtures of acrylated monomers such as those described in U.S. Pat. No. 4,652,274, the disclosure of which is incorporated herein by reference in its entirety; acrylated monomers such as those described in U.S. Pat. No. 4,642,126, the disclosure of which is incorporated herein by reference in its entirety; unsaturated amides such as methylene bis-arylamide, methylene bis-methacrylamide, 1,6-hexamethylene bis-acrylamide, diethylene triamine tris-acrylamide, and beta-methacrylaminoethyl methacrylate; and vinyl monomers such as styrene, diallyl phthalate, divinyl succinate, divinyl adipate, and divnylphthalate. Mixtures of two or more monomers can be used, if desired.

In some embodiments, the compositions include a hydroxy-containing material. Hydroxy-containing material, for example, can be an alcohol, a hydroxy-containing monomer, or combinations thereof. In some applications, hydroxy-containing materials tend to bleach the photopolymerizable composition; such bleached compositions often can be activated using ultraviolet light but not visible light.

The triarylsulfonium salt and arylsulfinate can both be selected to provide solubility in the monomer or monomer mixture. The triarylsulfonium and the arylsulfinate salts can be present in an amount effective to enable free radical polymerization of the ethylenically unsaturated monomers. The amount of each salt can affect the kinetics of the photopolymerization reaction. The rate of the polymerization reaction typically increases with an increased concentration of the salts.

In some applications, the triarylsulfonium salt and the arylsulfinate salt can each be present in an amount up to 4 weight percent based on the weight of the monomer. The amount of the salts can be the same or different. In some embodiments, the triarylsulfonium salt and the arylsulfinate salt are each present in an amount up to 3 weight percent, up to 2 weight percent, up to 1 weight percent, or up to 0.5 weight percent based on the weight of the monomers. For example, the triarylsulfonium salt and the arylsulfinate salt can each be present in an amount of 0.1 to 4 weight percent, 0.1 to 3 weight percent, 0.1 to 2 weight percent, or 0.5 to 1 weight percent based on the weight of the monomers.

Another aspect of the invention provides a composition that includes monomers capable of undergoing free radical polymerization reactions (i.e., ethylenically unsaturated monomers) and a triarylsulfonium arylsulfinate salt. The triarylsulfonium and arylsulfinate ions are the same as described above in more detail.

The compositions can contain a wide variety of additives depending on the desired use of the polymerized material. Suitable additives include solvents, diluents, resins, binders, plasticizers, inorganic and organic reinforcing or extending fillers, thixotropic agents, UV absorbers, medicaments, and the like. In some embodiments, these materials are chosen such that they do not competitively absorb actinic radiation that is needed to excite the arylsulfinate salts.

In some embodiments, the components of the compositions can be selected to provide a useful combination of cure speed, cure depth and shelf life. Some compositions can cure well even when loaded with large amounts of fillers. The compositions can be used to form foams, shaped articles, adhesives, filled or reinforced composites, abrasives, caulking and sealing formulations, casting and molding formulations, potting and encapsulating formulations, impregnating and coating formulations, and the like.

Suitable applications for the compositions include, but are not limited to, graphic arts imaging (e.g., for color proofing systems, curable inks, and silverless imaging), printing plates (e.g., for projection plates and laser plates), photoresists, solder masks for printed circuit boards, coated abrasives, magnetic media, photocurable adhesives (e.g., for orthodontics and general bonding applications), photocurable composites (e.g., for autobody repair and dental restoratives), protective coatings, and abrasion resistant coatings. The compositions are also suitable for use in a multi-photon process, where high intensity/short pulse lasers are used in combination with suitable dyes and co-reactants to produce polymerizable compositions that are useful for imaging, microreplication and stereolithographic applications. The compositions also can be used in other applications that are known to those skilled in the art.

Polymerization Methods

The invention also provides methods for photopolymerizing ethylenically unsaturated monomers using free radical polymerization reactions.

The photopolymerization method includes irradiating a photopolymerizable composition with actinic radiation until the photopolymerizable composition gels or hardens. The photopolymerizable composition includes monomers capable of undergoing free radical polymerization reactions (i.e., ethylenically unsaturated monomers) and a photoinitiator system. The photoinitiator system includes a triarylsulfonium salt and an arylsulfinate salt. In some applications of the photoinitiator systems, the components can be mixed together and stored for at least one day prior to use.

The arylsulfinate salt has an anion of Formula I $$Ar^1-SO_2^-  \qquad I$$

and a cation that contains at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. Suitable arylsulfinate salts are described above.

In some embodiments, the arylsulfinate salt has an anion that is a substituted benzenesulfinate, 1-naphthalenesulfinate, 2-naphthalenesulfinate, or 1-anthraquinonesulfinate and the cation is a tetraalkylammonium ion. A substituent on the arylsulfinate anion can be an electron withdrawing group or an electron withdrawing group in combination with an electron donating group. Exemplary arylsulfinates include, but are not limited to, tetrabutylammonium 4-chlorobenzenesulfinate, tetrabutylammonium 4-cyanobenzenesulfinate, tetrabutylammonium 4-ethoxycarbonylbenzenesulfinate, tetrabutylammonium 4-trifluoromethylbenzenesulfinate, tetrabutylammonium 3-trifluoromethylbenzenesulfinate, tetrabutylammonium 1-naphthalenesulfinate, tetrabutylammonium 2-naphthalenesulfinate, and tetrabutylammonium 1-anthraquinonesulfinate.

Other specific examples of arylsulfinate salts include, but are not limited to, 1-ethyl-3-methylimidazolium 4-cyanobenzenesulfinate, N,N-morpholinium 4-cyanobenzenesulfinate, 3-ethyl-2-methylbenxoxazolium 4-cyanobenzenesulfinate, 1-methyl-4-aza-1-azoniabicyclo [2.2.2]octane 4-cyanobenzenesulfinate and N-hexadecylpyridinium 4-cyanobenzenesulfinate.

The triarylsulfonium ion is often of Formula V

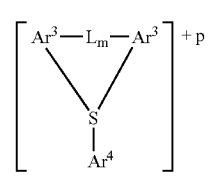

where each $Ar^3$ and $Ar^4$ are each independently a $C_{6-30}$ aryl or a $C_{3-30}$ heteroaryl that is unsubstituted or substituted; L is a divalent linking group selected from a single bond, oxo, thio, sulfinyl, carbonyl, sulfonyl, methylene, or imino, p is an integer equal to or greater than 1; and m is an integer equal to 0 or 1. The arylsulfonium ion can be unsubstituted or substituted with one or more substituents, each substituent having up to 30 carbon atoms and up to 10 heteroatoms selected from N, S, O, P, As, Si, Sb, B, or Ge. The substituents can be selected, for example, from alkyl, alkylcarbonyloxy, alkynyl, alkoxy, alkoxycarbonyl, alkylthio, arylthio, aralkyl, alkenyl, aryl, arylcarbonyloxy, arylcarbonylamido, alkylcarbonylamido, aryloxy, aryloxycarbonyl, alkoxysulfonyl, aryloxysulfonyl, alkylsulfonamido, N-alkylaminocarbonyl, N-arylaminocarbonyl, N-alkylsulfamyl, N-arylsulfamyl, alkylsulfonyl, arylsulfonyl, perfluoroalkyl, perfluoroalkysulfonyl, azo, boryl, halo, hydroxy, mercapto, diarylarsino, diarylstibino, trialkylgermano, trialkylsiloxy, or combinations thereof. Suitable triarylsulfonium salts are those described above in more detail.

Exemplary triarylsulfonium salts can have cation selected from

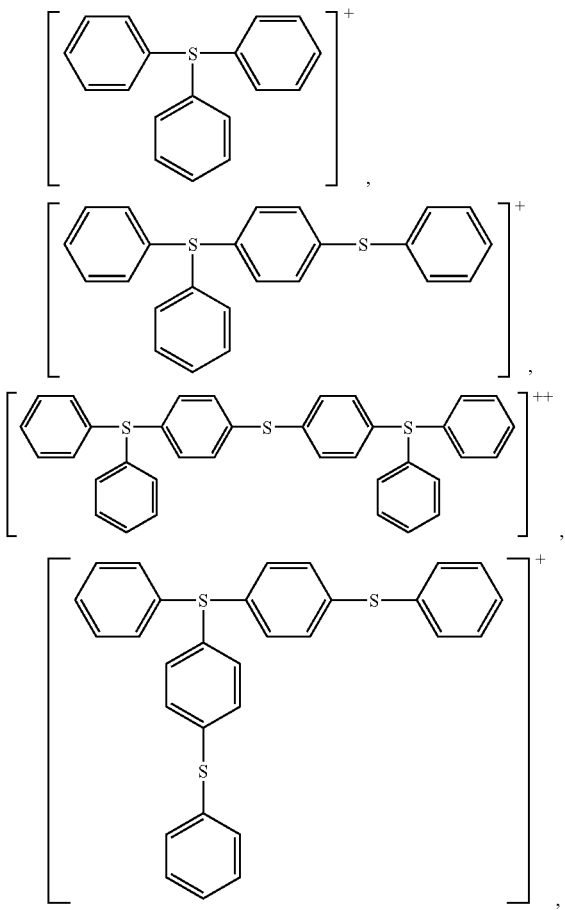

or combinations thereof that are unsubstituted or substituted with alkyl, alkylcarbonyloxy, alkynyl, alkoxy, alkoxycarbonyl, alkylthio, arylthio, aralkyl, alkenyl, aryl, arylcarbonyloxy, arylcarbonylamido, alkylcarbonylamido, aryloxy, aryloxycarbonyl, alkoxysulfonyl, aryloxysulfonyl, alkylsulfonamido, N-alkylaminocarbonyl, N-arylaminocarbonyl, N-alkylsulfamyl, N-arylsulfamyl, alkylsulfonyl, arylsulfonyl, perfluoroalkyl, perfluoroalkysulfonyl, azo, boryl, halo, hydroxy, mercapto, diarylarsino, diarylstibino, trialkylgermano, trialkylsiloxy, or combinations thereof. Suitable anions of the triarylsulfonium salts include, but are not limited to, $AsF_6^-$, $SbF_6^-$, $BF_4^-$, $PF_6^-$, $CF_3SO_3^-$, $HC(SO_2CF_3)_2^-$, $C(SO_2CF_3)_3^-$, $N(SO_2CF_3)_2^-$, tetraphenylborate, tetra(pentafluorophenyl)borate, and tetra(3,5-bis-trifluoromethylphenyl)borate, p-toluenesulfonate, and the like. In some embodiments, the anion is selected from $PF_6^-$, $AsF_6^-$, $SbF_6^-$, or combinations thereof.

Suitable monomers are those that are capable of free radical polymerization reactions and typically include ethylenically unsaturated monomers such as monoacrylates, monomethacrylates, diacrylates, dimethacrylates, polyacrylates, polymethacrylates, or combinations thereof.

The triarylsulfonium salts typically do not directly react with the arylsulfinate electron donors in the absence of actinic radiation, at least not at room temperature. The photoinitiator system can be activated by exposure of the photopolymerizable composition to actinic radiation. The actinic radiation typically has a wavelength of at least 250, at least 300, at least 325, at least 350, at least 400, at least 425, or at least 450 nanometers. The actinic radiation typically has a wavelength less than 1000, less than 900, less than 850, or less than 800 nanometers. For example, the actinic radiation can be in the range of about 250 to 1000 nanometers, in the range of 300 to 1000 nanometers, in the range of 350 to 1000 nanometers, in the range of 300 to 850 nanometers, in the range of 350 to 800 nanometers, in the range of 250 to 850 nanometers, in the range of 250 to 800 nanometers, in the range of 400 to 800 nanometers, in the range of 425 to 800 nanometers, or in the range of 450 to 800 nanometers.

Absorption of actinic radiation results in the formation of an initiating radical. The initiating radical reacts with an ethylenically unsaturated monomer to form a higher molecular weight radical that can react with other monomers resulting in the formation of yet higher molecular weight radicals leading to the formation of a polymeric material. In some instances, the polymeric material is cross-linked.

In some embodiments, visible light can be used to excite the arylsulfinate salt and activate the photoinitiator system. This can be advantageous because relatively inexpensive light sources can be used. Light sources emitting in the visible region of the electromagnetic spectrum tend to be less expensive than those emitting, for example, in the ultraviolet region. Other light sources that include ultraviolet radiation or a combination of ultraviolet and visible radiation can be used. Typical light sources include, but are not limited to, mercury vapor discharge lamps, carbon arcs, tungsten lamps, xenon lamps, sunlight, lasers, light emitting diodes, and the like.

Another aspect of the invention provides photopolymerization methods that include irradiating a photopolymerizable composition with actinic radiation until the photopolymerizable composition gels or hardens. The photopolymerizable composition includes monomers capable of undergoing free radical polymerization reactions (i.e., ethylenically unsaturated monomers) and a triarylsulfonium arylsulfinate salt.

In some embodiments, the triarylsulfonium arylsulfinate salt has an anion according to Formula I $$Ar^1-SO_2^- \qquad \qquad I$$

where $Ar^1$ is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. The cation of the triarylsulfonium arylsulfinate salt is according to Formula V

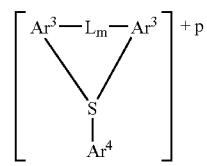

where each $Ar^3$ and $Ar^4$ are each independently a $C_{6-30}$ aryl or a $C_{3-30}$ heteroaryl that is unsubstituted or substituted; L is a divalent linking group selected from a single bond, oxo, thio, sulfinyl, carbonyl, sulfonyl, methylene, or imino; p is an integer equal to or greater than 1; and m is an integer equal to 0 or 1. The arylsulfonium ion can be unsubstituted or substituted with one or more substituents, each substituent having up to 30 carbon atoms and up to 10 heteroatoms selected from N, S, O, P, As, Si, Sb, B, or Ge. The substituents can be selected, for example, from alkyl, alkylcarbonyloxy, alkynyl, alkoxy, alkoxycarbonyl, alkylthio, arylthio, aralkyl, alkenyl, aryl, arylcarbonyloxy, arylcarbonylamido, alkylcarbonylamido, aryloxy, aryloxycarbonyl, alkoxysulfonyl, aryloxysulfonyl, alkylsulfonamido, N-alkylaminocarbonyl, N-arylaminocarbonyl, N-alkylsulfamyl, N-arylsulfamyl, alkylsulfonyl, arylsulfonyl, perfluoroalkyl, perfluoroalkysulfonyl, azo, boryl, halo, hydroxy, mercapto, diarylarsino, diarylstibino, trialkylgermano, trialkylsiloxy, or combinations thereof. Suitable triarylsulfonium ions are those described above in more detail.

The triarylsulfonium arylsulfinate salt can have a cation selected from

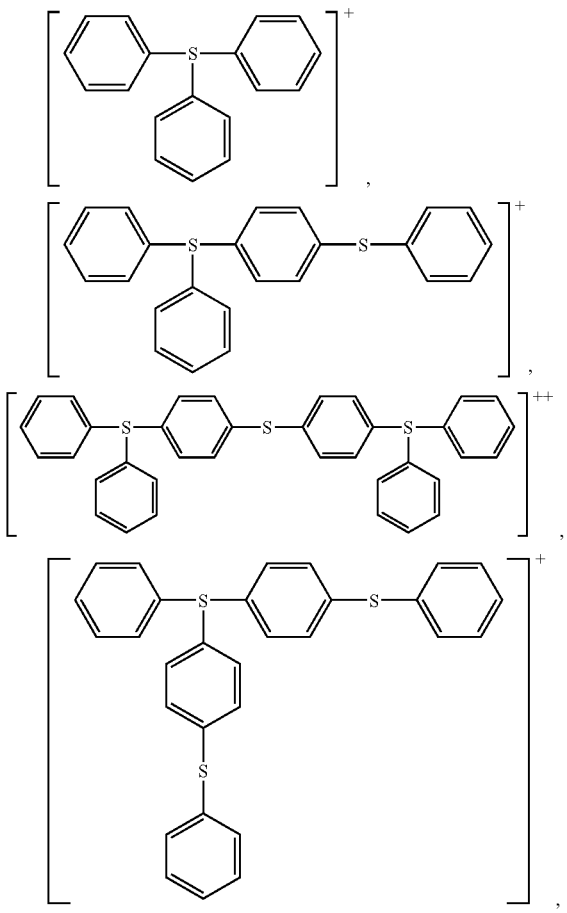

or combinations thereof that are unsubstituted or substituted with one or more substituents. Suitable substituents include alkyl, alkylcarbonyloxy, alkynyl, alkoxy, alkoxycarbonyl, alkylthio, arylthio, aralkyl, alkenyl, aryl, arylcarbonyloxy, arylcarbonylamido, alkylcarbonylamido, aryloxy, aryloxycarbonyl, alkoxysulfonyl, aryloxysulfonyl, alkylsulfonamido, N-alkylaminocarbonyl, N-arylaminocarbonyl, N-alkylsulfamyl, N-arylsulfamyl, alkylsulfonyl, arylsulfonyl, perfluoroalkyl, perfluoroalkysulfonyl, azo, boryl, halo, hydroxy, mercapto, diarylarsino, diarylstibino, trialkylgermano, trialkylsiloxy, or combinations thereof.

Exemplary anions of the triarylsulfonium arylsulfinate salt include a substituted benzenesulfinate, 1-naphthalenesulfinate, 2-naphthalenesulfinate, or 1-anthraquinonesulfinate, or combinations thereof. Substituents on the arylsulfinate include an electron withdrawing group or an electron withdrawing group in combination with an electron donating group. Electron donating groups can be selected, for example, from a primary amino, secondary amino, tertiary amino, hydroxy, alkoxy, aryloxy, alkyl, combinations thereof. Electron withdrawing groups can be selected, for example, from a halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

Exemplary arylsulfinate anions include, but are not limited to, 4-chlorobenzenesulfinate, 4-cyanobenzenesulfinate, 4-ethoxycarbonylbenzenesulfinate, 4-trifluoromethylbenzenesulfinate, 3-trifluoromethylbenzenesulfinate, 1-naphthalenesulfinate, 2-naphthalenesulfinate, and 1-anthraquinonesulfinate.

The photoinitiator system can be activated by exposure of the photopolymerizable composition to actinic radiation having a wavelength of at least 250, at least 300, at least 325, at least 350, at least 400, at least 425, or at least 450 nanometers. The actinic radiation typically has a wavelength less than 1000, less than 900, less than 850, or less than 800 nanometers. For example, the actinic radiation can be in the range of about 250 to about 1000 nanometers, in the range of 300 to 1000 nanometers, in the range of 350 to 1000 nanometers, in the range of 300 to 850 nanometers, in the range of 350 to 800 nanometers, in the range of 250 to 850 nanometers, in the range of 250 to 800 nanometers, in the range of 400 to 800 nanometers, in the range of 425 to 800 nanometers, or in the range of 450 to 800 nanometers.

Compounds

Another aspect of the invention provides triarylsulfonium arylsulfinate salts. The triarylsulfonium arylsulfinate salt has an anion of Formula I $$Ar^1-SO_2^-$$  I The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. Suitable $Ar^1$ groups for arylsulfinate ions of Formula I are described above.

Electron donating groups can be selected, for example, from a primary amino, secondary amino, tertiary amino, hydroxy, alkoxy, aryloxy, alkyl, or combinations thereof. Electron withdrawing groups can be selected, for example, from a halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

In some embodiments, the arylsulfinate ions of Formula I include, but are not limited to, 1-naphthalenesulfinate, 2-naphthalenesulfinate, and 1-anthraquinonesulfinate that are unsubstituted or substituted with an electron withdrawing group or an electron withdrawing group in combination with an electron donating group. In other embodiments, the triarylsulfonium arylsulfinate salt has an anion according to Formula IV

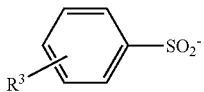
IV where $R^3$ is an electron withdrawing group selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof. The electron withdrawing group $R^3$ can be located, for example, in an ortho or para position of the benzene ring. Specific examples include 4-cyanobenzenesulfinate, 4-chlorobenzenesulfinate, 4-ethoxycarbonylbenzenesulfinate, and 4-trifluoromethylbenzenesulfinate. In other examples, $R^3$ can be located in a meta positions of the benzene ring. A specific example includes 3-trifluoromethylbenzenesulfinate.

Suitable triarylsulfonium ions are described above. The triarylsulfonium arylsulfinate salt typically has a cation according to Formula V

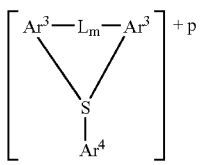
V where each $Ar^3$ and $Ar^4$ are each independently a $C_{6-30}$ aryl or a $C_{3-30}$ heteroaryl that is unsubstituted or substituted; L is a divalent linking group selected from a single bond, oxo, thio, sulfinyl, carbonyl, sulfonyl, methylene, or imino; p is an integer equal to or greater than 1; and m is an integer equal to 0 or 1. The arylsulfonium ion can be unsubstituted or substituted. The triarylsulfonium ion can be unsubstituted or substituted with one or more substituents, each substituent having up to 30 carbon atoms and up to 10 heteroatoms selected from N, S, O, P, As, Si, Sb, B, or Ge. Suitable substituents include alkyl, alkylcarbonyloxy, alkynyl, alkoxy, alkoxycarbonyl, alkylthio, arylthio, aralkyl, alkenyl, aryl, arylcarbonyloxy, arylcarbonylamido, alkylcarbonylamido, aryloxy, aryloxycarbonyl, alkoxysulfonyl, aryloxysulfonyl, alkylsulfonamido, N-alkylaminocarbonyl, N-arylaminocarbonyl, N-alkylsulfamyl, N-arylsulfamyl, alkylsulfonyl, arylsulfonyl, perfluoroalkyl, perfluoroalkysulfonyl, azo, boryl, halo, hydroxy, mercapto, diarylarsino, diarylstibino, trialkylgermano, trialkylsiloxy, or combinations thereof.

In some embodiments, the triarylsulfonium ion is selected from

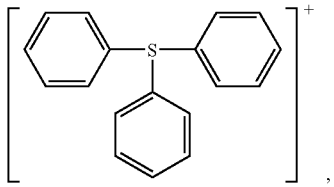

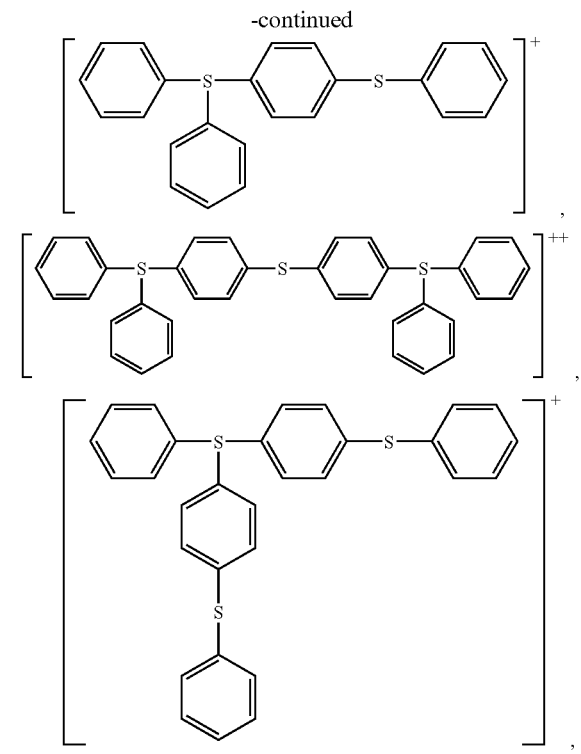

or combinations thereof that are unsubstituted or substituted with one or more substituents. Suitable substituents include alkyl, alkylcarbonyloxy, alkynyl, alkoxy, alkoxycarbonyl, alkylthio, arylthio, aralkyl, alkenyl, aryl, arylcarbonyloxy, arylcarbonylamido, alkylcarbonylamido, aryloxy, aryloxycarbonyl, alkoxysulfonyl, aryloxysulfonyl, alkylsulfonamido, N-alkylaminocarbonyl, N-arylaminocarbonyl, N-alkylsulfamyl, N-arylsulfamyl, alkylsulfonyl, arylsulfonyl, perfluoroalkyl, perfluoroalkysulfonyl, azo, boryl, halo, hydroxy, mercapto, diarylarsino, diarylstibino, trialkylgermano, trialkylsiloxy, or combinations thereof.

Specific compounds include, but are not limited to, triphenylsulfonium 4-cyanobenzenesulfinate, triphenylsulfonium 4-cyanobenzenesulfinate, triphenylsulfonium 4-ethoxycarbonylbenzenesulfinate, triphenylsulfonium 4-trifluoromethylbenzenesulfinate, triphenylsulfonium 3-trifluoromethylbenzenesulfinate, triphenylsulfonium 1-naphthalenesulfinate, triphenylsulfonium 2-naphthalenesulfinate, and triphenylsulfonium 2-anthraquinonesulfinate.

The triarylsulfonium arylsulfinate salts typically have a solubility of at least 0.05 moles/liter, at least 0.07 moles/liter, at least 0.08 moles/liter, at least 0.09 moles/liter, or at least 0.1 moles/liter in a variety of solvents and ethylenically unsaturated monomers. Thus, the triarylsulfonium arylsulfinate salts are often not limited to applications that include aqueous formulations or aqueous systems with a large amount (e.g., 30 to 70 weight percent) of a cosolvent such as an alcohol.

The triarylsulfonium arylsulfinate salt can be activated by exposure to actinic radiation having a wavelength in the range of 250 to 1000 nanometers, in the range of 300 to 1000 nanometers, in the range of 350 to 1000 nanometers, in the range of 250 to 850 nanometers, in the range of 250 to 800 nanometers, in the range of 400 to 800 nanometers, in the range of 425 to 800 nanometers, or in the range of 450 to 800 nanometers. Although not intending to be bound by theory, it is believed that the arylsulfinate ion typically absorbs actinic radiation to form an excited arylsulfinate ion. The excited arylsulfinate ion can transfer an electron to the triarylsulfonium ion resulting in the formation of an arylsulfinate radical. The arylsulfinate radical typically can photodegrade and form a radical that can initiate free radical polymerization reactions.

In some embodiments, the triarylsulfonium arylsulfinate salts can be stored as a neat compound at room temperature without undergoing oxidative degradation. For example, some of the triarylsulfonium arylsulfinate salts can be stored for greater than one day, greater than 2 days, greater than 1 week, greater than 2 weeks, or greater than 1 month. The time required to oxidize 50 percent of the compound ($t_{1/2}$) at room temperature (i.e., 20° C. to 25° C.) can be used to compare the relative ease of oxidative degradation of various triarylsulfonium arylsulfinate salts. The $t_{1/2}$ is calculated based on pseudo-first order kinetics as described in K. A. Connors, Chemical Kinetics: The Study of Reaction Rates in Solution, chapter 2, VCH, New York, 1990.

EXAMPLES

Unless otherwise noted:

the solvents and reagents were or can be obtained from Aldrich Chemical Co., Milwaukee, Wis. or may be synthesized by known methods;

electrochemical instrumentation for cyclic voltammetry was obtained from Princeton Applied Research, Oak Ridge, Tenn.;

N,N-dimethylformamide was obtained from EM Science, Gibbstown, N.J.;

as used herein, the term "SR339" refers to 2-phenoxyethyl acrylate and was obtained from Sartomer Co., Inc., Exton, Pa.;

as used herein, the term SR238 refers to 1,6-hexanediol diacrylate and was obtained from Sartomer Co., Inc.

triarylsulfonium chloride was obtained as an aqueous solution from Aceto Corp., Lake Success, N.Y.

Measurement of Oxidation Potentials

The electrochemical measurements of the exemplary arylsulfinates were made using an EG&G PARC Model 175 Universal Programmer, interfaced to a Princeton Applied Research Model 173 potentiostat/galvanostat fitted with a Princeton Applied Research Model 179 Digital Coulometer and Model 178 Electrometer. The signal was digitized using a Model DI-151R5 Waveform Recording System (available from DATAQ Instruments, Inc., Akron, Ohio) and then stored and analyzed on a Dell OptiPlex XM 590 pc. Scans were run at 100 mV/sec scan rate.

The electrochemical measurements were made using a three-electrode configuration: a reference electrode, a working electrode, and a counter electrode. The reference electrode was a fritted electrode (obtained from Sargent Welch, Buffalo Grove, Ill.) that was filled with 0.01M $AgNO_3$ in acetonitrile and fitted with a silver wire 1 mm in diameter by approximately 19 cm in length. The counter electrode was a platinum wire 1.0 mm in diameter and approximately 16 cm long (overall length) formed into a coil having a coil diameter of approximately 10 mm and a coil length of about 7.5 cm. The working electrode was a glassy carbon electrode, approximately 3.5 mm in diameter (obtained from BAS, Inc., West Lafayette, Ind.). The glassy carbon electrode was polished using first a 3.0 micron aluminum oxide powder/deionized water slurry, then a 0.3 micron alpha alumina powder/deionized water slurry. The polishing powders were obtained from Buehler LTD, Evanston, Ill.

The cell was a 50 mL four neck round bottom flask. Each electrode was sealed in to the flask using the appropriately sized rubber septum. The fourth inlet was used to introduce an argon purge to remove oxygen and keep atmospheric moisture out of the cell.

The supporting electrolyte was tetrabutylammonium hexafluorophosphate (TBA $PF_6$) (obtained from Southwestern Analytical Chemicals, Inc., Austin, Tex.). The TBA $PF_6$ was dried overnight in a vacuum oven at 80-90° C. before each experiment. The solvent was N,N-dimethylformamide (DMF), and it was used as received without further purification. The solvent was transferred to the electrochemical cell via syringe under an argon atmosphere to minimize atmospheric moisture uptake.

Electrochemical measurements were made by first preparing a 0.1 molar solution of TBA $PF_6$ in DMF. This solution was added to the cell, which contained a small magnetic stir bar, as argon gas was flowing through the cell. After the reference and counter electrodes were connected to the instrumentation, the working electrode was polished as described above and was then inserted into the cell. A background scan was conducted before the exemplary compounds were added to the cell. Then, approximately 10 mg of the compound was added to the cell and, after it had dissolved, the measurement was made to record the oxidation potential. The potential was determined as the voltage at peak current on the first scan. In this configuration, the oxidation potential of ferrocene in an identical electrolyte solution appeared at +0.1 volts versus the reference electrode.

Preparation of Triarylsulfonium Salts

Triarylsulfonium hexafluorophosphate and triarylsulfonium hexafluoroantimonate were prepared using a metathesis procedure in which the commercially available aqueous triarylsulfonium chloride solution was mixed with an aqueous solution of an alkali metal or an ammonium hexafluorophosphate or antimonate. The mixture was then extracted with methylene chloride and the extract was dried over a solid drying agent such as $CaSO_4$ and was then concentrated to dryness using a rotary evaporator. The products were further dried using a vacuum oven.

Preparative Example 1

Preparation of 4-Cyanobenzenesulfonyl Chloride

An intimate mixture of 4-carboxybenzenesulfonamide (188 g) and $PCl_5$ (430 g) was made by combining the solids in a resealable plastic bag and manually kneading and shaking the bag. The mixture was transferred to a round bottom flask that was fitted with a magnetic stir bar and a hose adapter connected to a source of nitrogen gas. The flask was slowly heated to 60° C. in an oil bath and was held at 60° C. for 5 hours as the mixture was stirred. The hose adapter was then connected to a water aspirator through a trap that was cooled with dry ice and the temperature of the oil bath was increased to 110° C. while the flask was evacuated and liquid distilled into the trap. When the rate of distillation slowed, the hose adapter was again connected to the nitrogen source and the temperature of the oil bath was raised to 155° C. After an additional 13 hours, the hose adapter was again connected to a water aspirator through a trap and more liquid was distilled. The reaction flask was then allowed to cool to room temperature, during which time the brown product solidified. The crude product was vacuum distilled, using a Kugelrhor distillation apparatus at a temperature of 150° C. and a pressure of 0.07 mmHg, into a collection bulb that was cooled in an ice bath. The solid yellow distillate was washed from the collection bulb with $CH_2Cl_2$ and that solution was concentrated to dryness with a rotary evaporator to afford 167.4 g of product.

Preparative Example 2

Preparation of Potassium 4-Ethoxycarbonylbenzenesulfonate

A mixture of sodium 4-carboxybenzenesulfonate (75 g) in deionized water (1200 mL) was heated to 60° C. until the solid was dissolved. This solution was passed through a column of a strongly acidic ion-exchange resin (available under the trade designation AMBERLITE IR-120(PLUS) from Rohm and Haas Co., Philadelphia, Pa.) that had been acidified by washing sequentially with deionized water, concentrated HCl and deionized water until the pH of the eluate was approximately 5.5. The column was then washed with deionized water until a total of 2L of eluate was collected. The deionized water was removed with a rotary evaporator and the resultant intermediate was dried in a vacuum oven overnight at 50° C.

The intermediate was then dissolved in 1L of anhydrous ethanol in a round bottom flask fitted with a magnetic stir bar, a condenser and a hose adapter that was attached to a source of nitrogen gas. This solution was stirred and heated overnight in an oil bath at 100° C. An additional 500 mL of ethanol was added to the flask and heating and stirring was continued for an additional 4 hours. The solution was allowed to cool to room temperature and was neutralized with alcoholic KOH to the bromothymol blue endpoint. The product precipitated from the solution and was isolated by vacuum filtration and was washed with anhydrous ethanol. The solid was dried overnight at room temperature to afford 75.1 g of product.

Preparative Example 3

Preparation of 4-Ethoxycarbonylbenzenesulfonyl Chloride

A round bottom flask, fitted with a magnetic stir bar and a hose adapter connected to a source of nitrogen gas, was charged with a solution of potassium 4-ethoxycarbonylbenzenesulfonate (75.1 g) dissolved in a 3:1 (v/v) mixture of acetonitrile (300 mL) and sulfolane (100 mL). As the solution was stirred, $POCl_3$ (55 mL) was added slowly and the stirring mixture was heated at 75° C. under a nitrogen atmosphere for 3 hours. The heterogeneous reaction mixture was allowed to cool to room temperature and was then concentrated using a rotary evaporator. The flask was then cooled in an ice bath and ice was added to the mixture in the flask. The product crystallized as a white solid and was filtered and washed with cold deionized water. The product was dried under vacuum at room temperature and 3 mmHg for 2 hours to afford 76 g of white solid.

Preparative Examples 4-5

Preparation of Substituted Sodium Benzenesulfinates

Sodium benzenesulfinates were prepared by hydrolysis of the substituted benzenesulfonyl chlorides that were prepared as described in Preparative Examples 1 and 2. Each substituted benzenesulfonyl chloride was stirred for 3 hours at 75° C. in deionized water, at a concentration of 0.2 g of substituted benzenesulfonyl chloride per milliliter of deionized water, with 2.5 equivalents of $Na_2SO_3$ and 2.5 equivalents of $NaHCO_3$ in a round bottom flask. Each reaction mixture was then allowed to cool to room temperature and was then cooled in a refrigerator to 10° C. Each cold solution was acidified with concentrated sulfuric acid until the pH was less than 1.

Each precipitated solid was extracted into ethyl acetate and then the organic phase was evaporated to dryness using a rotary evaporator to afford the substituted benzenesulfinic acid as a colorless solid. Each of the solid substituted benzenesulfinic acids was dissolved in methanol to give approximately 10 weight percent solutions. Deionized water was then added dropwise to each solution until a precipitate just formed. Sufficient methanol was then added to the solution until all of the solid dissolved. Each aqueous methanol solution was neutralized with a 1M aqueous solution of alkali metal hydroxide, as indicated in Table 1, to afford the alkali metal salt of the substituted benzenesulfinate, which was isolated by removal of the solvent with a rotary evaporator. The data are given in Table 1.

TABLE 1

| Preparative Examples 4-5 | | | | |
|---|---|---|---|---|
| Preparative Example | Benzenesulfonyl chloride | Wt. Benzenesulfonyl chloride | MOH | Wt. Benzenesulfinate |
| 4 | 4-Cyano | 11.68 g | NaOH | 9.30 g |
| 5 | 4-Ethoxycarbonyl | 6.46 g | LiOH | 5.35 g |

Preparative Examples 6-7

Preparation of Substituted Tetrabutylammonium Benzenesulfinates

Tetrabutylammonium benzenesulfinate were prepared from the corresponding alkali metal sulfinates. Each alkali metal sulfinate was dissolved in deionized water to give a 0.1M solution that was acidified with concentrated sulfuric acid to afford the sulfinic acid as a colorless precipitate. Each mixture was extracted into ethyl acetate and then the organic solution was evaporated to dryness using a rotary evaporator. Each resultant solid was dissolved in 50% (v/v) aqueous methanol and this solution was titrated with an aqueous solution of tetrabutylammonium hydroxide. Each mixture was evaporated to dryness using a rotary evaporator to afford the product as a yellow oil. The $^1H$ and $^{13}C$ NMR spectra of each compound were consistent with the assigned structure. Details of these preparations and the oxidation potential of each compound are given in Table 2.

TABLE 2

| Preparative Examples 6-7 | | |
|---|---|---|
| | Preparative Example | |
| | 6 | 7 |
| Alkali Metal Benzenesulfinate | 4-Cyano | 4-Ethoxycarbonyl |
| Wt. Alkali Metal Benzenesulfinate | 2.00 g | 0.58 g |
| Wt. Tetrabutylammonium Benzenesulfinate | 4.18 g | 1.27 g |
| $E_{ox}$ | 0.15 V | 0.11 V |

Preparative Example 8

Preparation of Tetrabutylammonium Naphthalene-1-sulfinate

A round bottom flask was charged with 20.0 g 1-naphthalenesulfonyl chloride, 33.36 g $Na_2SO_3$, 22.24 g $NaHCO_3$ and 350 mL deionized water. The mixture was stirred and heated to 65° C. under a nitrogen atmosphere for 2 hours, after which time the mixture was allowed to cool to room temperature and was then further cooled in a refrigerator. The cold mixture was acidified with concentrated $H_2SO_4$ which resulted in the formation of a precipitate. The mixture was extracted three times with 100 mL of ethyl acetate. The organic extracts were combined and the solvent was removed with a rotary evaporator to give a colorless solid that was immediately dissolved in 240 mL of 1:1 (v/v) methanol-deionized water in a beaker. The solution was titrated with a solution of 40% aqueous tetrabutylammonium hydroxide until the pH of the solution was 7.2. The solvent was removed with a rotary evaporator and the product was further dried in a vacuum oven at room temperature to afford 36.4 g of a yellow waxy solid.

Preparative Example 9

Preparation of Tetrabutylammonium Naphthalene-2-sulfinate

A round bottom flask was charged with 24.73 g of 2-naphthalenesulfonyl chloride, 41.25 g $Na_2SO_3$, 41.25 g $NaHCO_3$ and 350 mL deionized water. The mixture was stirred and heated to 65° C. under a nitrogen atmosphere for 2 hours, after which time the mixture was allowed to cool to room temperature and was then further cooled in a refrigerator. The cold mixture was acidified with concentrated $H_2SO_4$, which resulted in the formation of a precipitate.

The mixture was extracted three times with 100 mL of ethyl acetate. The organic extracts were combined and the solvent was removed with a rotary evaporator to give a colorless solid that was immediately dissolved in 240 mL of 1:1 (v/v) methanol-deionized water in a beaker. The solution was titrated with a solution of 40% aqueous tetrabutylammonium hydroxide until the pH of the solution was 7.2. The solvent was removed with a rotary evaporator and the product was further dried in a vacuum oven at room temperature to afford 46.9 g of a yellow waxy solid.

Preparative Example 10

Preparation of Triphenylsulfonium Hexafluoroantimonate

A 500 mL 3-neck round bottom flask, fitted with a mechanical stirrer, thermometer and reflux condenser with a drying tube, was charged with diphenyl sulfoxide (20.2 g) and benzene (200 mL). To the stirred mixture was added $AlCl_3$ (80.1 g) in several portions and this mixture was stirred and heated to reflux for 23 hours. The reaction mixture was then allowed to cool to room temperature and was slowly poured into a mixture of concentrated aqueous HCl (150 mL) and ice in a beaker. This mixture was then filtered and the aqueous layer of the filtrate was separated. The aqueous layer was extracted four times with benzene (50 mL). The aqueous phase was separated and was transferred to a flask that was fitted with a magnetic stir bar. While the aqueous solution was vigorously stirred, $NaSbF_6$ (28.5 g) was added to the flask in several portions. The resultant precipitate was filtered, washed with deionized water and dried in air for 3 days to afford 14.0 g of product.

Examples 1-2

Photopolymerization Using Triarylsulfonium Salts with Substituted Benzenesulfinate Salts Two separate mixtures of SR339, each with 1 weight percent each of triarylsulfonium hexafluoroantimonate and the substituted tetrabutylammonium benzenesulfinate of Preparative Examples 6 or 7, were prepared. For Example 1, 1.1 weight percent of tetrabutylammonium 4-cyanobenzenesulfinate was used, whereas for Example 2, 1.0 weight percent of tetrabutylammonium 4-ethoxycarbonylbenzenesulfinate was used. Each sample was evaluated for rate and extent of cure by photo differential scanning calorimetry (photo-DSC) using a model DSC2920 calorimeter (available from TA Instruments, New Castle, Del.) with light from a 100 W medium pressure mercury that was filtered through a Model GG400 long pass filter (available from Esco Products, Oak Ridge, N.J.). The results are given in Table 3.

TABLE 3

Curing of Examples 1-2

| Example | Substituted tetrabutyl-ammonium benzene-sulfinate | Initial Slope (W/g-min) | Time to peak maximum (min) | Total evolved heat (J/g) |
|---|---|---|---|---|
| 1 | 4-Cyano | 32.8 | 0.41 | 363.6 |
| 2 | 4-Ethoxy-carbonyl | 21.3 | 0.47 | 314.7 |

Comparative Example 1

Photopolymerization Using Triarylsulfonium Hexafluoroantimonate

A mixture of SR339 and 1 weight percent of $Ar_3S^+SbF_6^-$ was prepared. The sample was evaluated for rate and extent of cure by photo differential scanning calorimetry (photo-DSC) using a model DSC2920 calorimeter (available from TA Instruments, New Castle, Del.) with light from a 100 W medium pressure mercury lamp that was filtered through a Model GG400 long pass filter (available from Esco Products, Oak Ridge, N.J.). The results are given in Table 4.

TABLE 4

Curing of Comparative Example 1

| Comparative Example | Initial Slope (W/g-min) | Time to peak maximum (min) | Total evolved heat (J/g) |
|---|---|---|---|
| 1 | 0 | 0 | 0 |

Comparative Examples 2-3

Photopolymerization Using Substituted Tetrabutylammonium Benzenesulfinates

Two separate mixtures of SR339, each with 1.0 weight percent of the tetrabutylammonium benzenesulfinate of Preparative Examples 6 or 7, were prepared. Each sample was evaluated for rate and extent of cure by photo differential scanning calorimetry according to the method of Comparative Example 1. The results are given in Table 5.

TABLE 5

Curing of Comparative Examples 2-3

| Comparative Example | Substituted tetrabutyl-ammonium benzene-sulfinate | Initial Slope (W/g-min) | Time to peak maximum (min) | Total evolved heat (J/g) |
|---|---|---|---|---|
| 2 | 4-Cyano | 0 | 0 | 0 |
| 3 | 4-Ethoxy-carbonyl | 0 | 0 | 0 |

Example 3

Bulk Photopolymerization Using Broad Spectrum Light and a Triarylsulfonium Salt with a Substituted Benzenesulfinate Salt A mixture of SR339 with 1.0 weight percent of triarylsulfonium hexafluorophosphate and 1.0 weight percent of tetrabutylammonium 4-cyanobenzenesulfinate was prepared in a screw-cap vial. The mixture was purged with nitrogen gas for 45 seconds and then the vial was sealed and the sample was irradiated with a 100 W quartz-tungsten-halogen (QTH) light source (model I-100, available Cuda Fiberoptics, Jacksonville, Fla.) by holding and slowly agitating the vial approximately 2 cm in front of the light source. The light source shutter was fully open. Cure time was considered to be the time that it took for the solution viscosity to increase so that the liquid no longer flowed in the vial as the vial was agitated. The mixture was cured in 5 seconds.

Comparative Example 4

Bulk Photopolymerization Using Broad Spectrum Light and A Triarylsulfonium Salt Without A Benzenesulfinate Salt A mixture of SR339 with 1.0 weight percent of triarylsulfonium hexafluorophosphate was prepared in a screw-cap vial. The mixture was purged with nitrogen gas for 45 seconds and then the vial was sealed and the sample was irradiated as described in Example 3. Cure time was considered to be the time that it took for the solution viscosity to increase so that the liquid no longer flowed in the vial as the vial was agitated. The mixture was cured in 24 seconds.

Example 4

Bulk Photopolymerization Using Blue Light and A Triarylsulfonium Salt with A Substituted Benzenesulfinate Salt A mixture of SR339 with 1.0 weight percent of triarylsulfonium hexafluorophosphate and 1.0 weight percent of tetrabutylammonium 4-cyanobenzenesulfinate, was prepared in a screw-cap vial. The mixture was purged with nitrogen gas for 45 seconds and the sample was irradiated with a Model 5560 dental curing light (obtained from 3M Company, St. Paul, Minn.) by holding and slowly agitating the vial approximately 2 cm in front of the light source. Cure time was considered to be the time that it took for the solution viscosity to increase so that the liquid no longer flowed in the vial as the vial was agitated. The mixture was cured in 40 seconds.

Comparative Example 5

Bulk Photopolymerization Using Blue Light and A Triarylsulfonium Salt without A Substituted Benzenesulfinate Salt A mixture of SR339 with 1.0 weight percent of triarylsulfonium hexafluorophosphate was prepared in a screw-cap vial. The mixture was purged with nitrogen gas for 45 seconds and then the vial was sealed and the sample was irradiated as described in Example 4. Cure time was considered to be the time that it took for the solution viscosity to increase so that the liquid no longer flowed in the vial as the vial was agitated. The mixture did not cure. After 40 seconds the mixture still flowed in the vial.

Example 5

Preparation of Triarylsulfonium 4-Cyanobenzenesulfinate

The commercially available aqueous solution of triarylsulfonium chloride was dried using a rotary evaporator and then a vacuum oven. A mixture of dry triarylsulfonium chloride (1.0 g) and anhydrous ethanol (10 mL) was magnetically stirred at 40° C. for one hour. The mixture was then filtered through a pad of a filter aid (available under the trade designation CELITE from Aldrich Chemical Co., Milwaukee Wis.) in a fritted glass filter funnel. To the filtrate was added a solution of sodium 4-cyanobenzenesulfinate (0.52 g) in anhydrous ethanol (10 mL) and this mixture was magnetically stirred at room temperature for 1 hour. The mixture was filtered and the solvent was removed using a rotary evaporator. The residue was dissolved in methylene chloride and this solution was filtered. The solvent was removed using a rotary evaporator to afford 1.54 g of product as a hygroscopic solid.

Examples 6-7

Photopolymerization Using Triarylsulfonium 4-Cyanobenzenesulfinate

Two separate mixtures of SR339, each with 1 weight percent each of triarylsulfonium 4-cyanobenzenesulfinate, were prepared. Each sample was evaluated for rate and extent of cure by photo differential scanning calorimetry (photo-DSC) using a model DSC2920 calorimeter (available from TA Instruments, New Castle, Del.) with light from a 100 W medium pressure mercury that was either unfiltered or was filtered through a Model GG400 long pass filter (available from Esco Products, Oak Ridge, N.J.) according to the data in Table 3. The results are given in Table 3.

TABLE 3

Curing of Examples 6-7

| Example | Filter | Initial Slope (W/g-min) | Time to peak maximum (min) | Total evolved heat (J/g) |
|---|---|---|---|---|
| 6 | None | 209.5 | 0.13 | 359.8 |
| 7 | GG400 | 33.2 | 0.33 | 335.3 |

Example 8

Bulk Photopolymerization Using Triphenylsulfonium Hexafluoroantimonate and Tetrabutylammonium Naphthalene-1-sulfinate A mixture of SR238 with 1.0 weight percent of triphenylsulfonium hexafluoroantimonate and 1.0 weight percent of tetrabutylammonium naphthalene-1-sulfinate was prepared in a screw-cap vial. The solution was purged with nitrogen gas for 45 seconds and then vial was sealed and the sample was irradiated as described in Example 4. The mixture was cured in 6 seconds.

Example 9

Bulk Photopolymerization Using Triphenylsulfonium Hexafluoroantimonate and Tetrabutylammonium Naphthalene-2-sulfinate A mixture of SR238 with 1.0 weight percent of triphenylsulfonium hexafluoroantimonate and 1.0 weight percent of tetrabutylammonium naphthalene-2-sulfinate was prepared in a screw-cap vial. The solution was purged with nitrogen gas for 45 seconds and then vial was sealed and the sample was irradiated as described in Example 4. The mixture was cured in 7 seconds.

Examples 10-13

Photopolymerization Using Triphenylsulfonium Hexafluoroantimonate and Tetrabutylammonium Naphthalenesulfinates Four separate mixtures of SR339, each with 1 weight percent of propylene carbonate and 1 weight percent each of the naphthalene sulfinates of Preparative Examples 8 or 9, were prepared. For Examples 10 and 11, triphenylsulfonium naphthalene-1-sulfinate was used, whereas for Examples 12 and 13, triphenylsulfonium naphthalene-2-sulfinate was used. Each sample was evaluated for rate and extent of cure by photo differential scanning calorimetry (photo-DSC) using the method of Examples 6-7. The results are given in Table 4.

TABLE 4

Curing of Examples 10-13

| Example | Tetrabutyl-ammonium Naphthalene sulfinate | Filter | Initial Slope (W/g-min) | Time to peak maximum (min) | Total evolved heat (J/g) |
|---|---|---|---|---|---|
| 10 | Naphthalene-1-sulfinate | None | 381 | 0.09 | 420 |
| 11 | Naphthalene-1-sulfinate | GG400 | 14.2 | 0.47 | 383 |
| 12 | Naphthalene-2-sulfinate | None | 242 | 0.10 | 388 |
| 13 | Naphthalene-2-sulfinate | GG400 | 0.15 | 0.81 | 277 |

What is claimed is:

1. A method of photopolymerization comprising irradiating a photopolymerizable composition with actinic radiation until the photopolymerizable composition gels or hardens, said photopolymerizable composition comprising:

an ethylenically on saturated monomer;

an arylsulfinate salt having an anion of Formula I

and having a cation that contains at least one carbon atom and either a positively charged nitrogen atom or a positively charged phosphorus atom, wherein $Ar^1$ is a substituted phenyl, an unsubstituted or substituted $C_{7-30}$ aryl or an unsubstituted or substituted $C_{3-30}$ heteroaryl, said substituted $Ar^1$ having a substituent that is an electron withdrawing group or an electron withdrawing group in combination with an electron donating group; and a triarylsulfonium salt, wherein the polymerizable composition generates a radical upon exposure to actinic radiation and wherein the photopolymerizable composition is free of an additive that competitively absorbs actinic radiation.

2. The method of claim 1, wherein the actinic radiation is in the range of 250 to 1000 nanometers.

3. The method of claim 1, wherein the actinic radiation is in the range of 250 to 850 nanometers.

4. The method of claim 1, wherein the arylsulfinate salt has an anion that is a benzenesulfinate substituted with an electron withdrawing group selected front halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkysulfonyl, alkylsulfonyl, azo, alkenyl, alkynyl, dialkylphosphonato, diarylphosphonato, aminocarbonyl, or combinations thereof.

5. The method of claim 1, wherein the $Ar^1$ group of the arylsulfinate salt is naphthyl or anthraquinonyl that is unsubstituted or substituted with an electron withdrawing group or an electron withdrawing group in combination with an electron donating group.

6. The method of claim 1, wherein the cation of the arylsulfinate salt is of Formula II

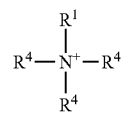

where
$R^1$ is an unsubstituted alkyl, an alkyl substituted with a hydroxy, an unsubstituted aryl, or an aryl substituted with an alkyl, hydroxy, or combinations thereof; and
each $R^4$ is independently hydrogen, an unsubstituted alkyl, an akyl substituted with a hydroxy, an unsubtituted aryl, or an aryl substituted with an alkyl, alkoxy, or combination thereof.

7. The method of claim 1, wherein the arylsulfinate salt has a cation that is a tetralkylammonium ion, wherein each alkyl group has 4 to 30 carbon atoms.

8. The method of claim 1, wherein the cation of the arylsulfinate salt is of Formula III

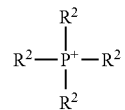

where each R² is independently an unsubstituted alkyl, an alkyl substituted with a hydroxy, an unsubstituted aryl, or an aryl substituted with an alkyl, hydroxy, or combinations thereof.

9. The method of claim 1 wherein the cation of the arylsulfinate salt is a ring structure comprising a 4 to 12 member heterocyclic group having a positively charged nitrogen atom, said heterocyclic being saturated or unsaturated and having up to 3 heteroatoms selected from oxygen, sulfur, nitrogen, or combinations thereof, wherein said ring structure is unsubstituted or substituted with a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof.

10. The method of claim 1, wherein the triarylsulfonium salt has a cation according to Formula V

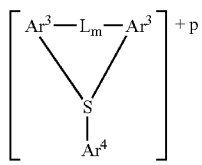
V wherein
each Ar³ and Ar⁴ are independently a $C_{6-30}$ aryl or a $C_{3-30}$ heteroaryl that is substituted or substituted with one or more substituents, each substituent having up to 30 carbon atoms and up to 10 heteroatoms selected from N, S, O, P, As, Si, Sb, B, or Ge; and L is a divalent linking group selected from a single bond, oxo, thio, sulfinyl, carbonyl, sulfonyl, methylene, or imino;

p is an integer equal to or greater than 1; and m in is an integer equal to 0 or 1.

11. The method of claim 1, wherein the triarylsulfonium salt has a cation selected from

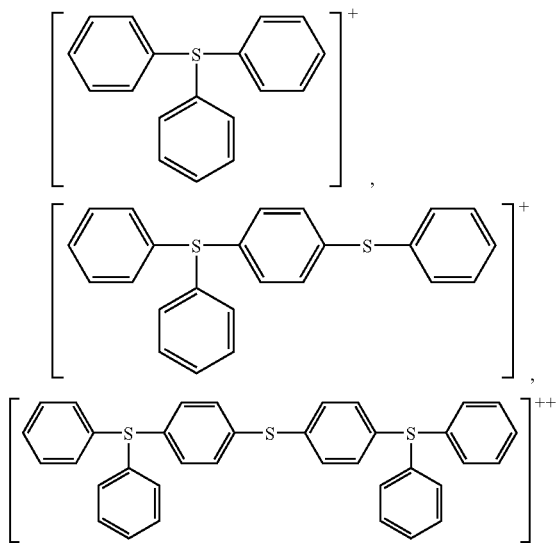

-continued

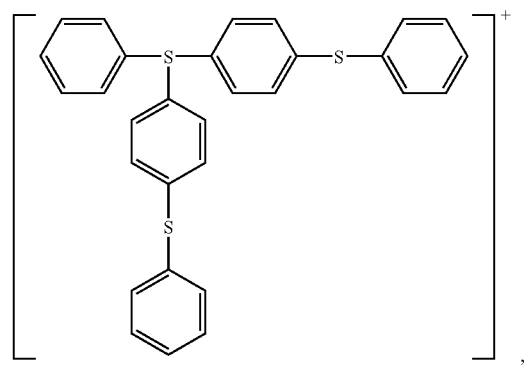

or combinations thereof that are unsubstituted or substituted with one or more substituents selected from alkyl, alkylcarbonyloxy, alkynyl, alkoxy, alkoxycarbonyl, alkylthio, arylithio, aralkyl, alkenyl, aryl, arylcarbonyloxy, arylcarbonylamido, alkylcarbonylamido, aryloxy, aryloxycarbonyl, alkoxysulfonyl, aryloxysulfonyl, alkysulfonamido, N-alkylaminocarbonyl, N-arylaminocarbonyl, N-alkylsulfamyl, N-arylsulfamyl, alkysulfonyl, arylsulfonyl, perfluoroalkyl, perfluoroalkysulfonyl, azo, boryl, halo, hydroxy, mercapto, diarylarsino, diarystibino, trialylgermano, trailkylsiloxy, or combinations thereof.

12. The method of claim 1, wherein the triarylsufomium salt has a cation that is triphenylsulfonium, diphenylmaphthylsulfonium, tritolysulfonium, anisyldiphenylsulfonuim, 4-butoxyphenyldipenylsulfonium, 4-tert-butylphenyldiphenylsulfonuim, 4-chlorophenyldiphenylsulfonuim, tris(4-phenoxyphenyl)sulfonuim, 4-acetonylphenyldiphenylsulfonium, or tris(4-thiomethoxyphenyl)sulfonuim, or 4-acetamidophenyldiphenylsulfonium.

13. The method of claim 1, wherein the triarylsulfonium salt has an anion that is selected from $AsF_6^-$, $SbF_6^-$, $PF_6^-$, $CF_3SO_3^-$, $HC(SO_2CF_3)_2^-$, $C(SO_2CF_3)_3^-$, $N(SO_2CF_3)_2^-$, tetraphenylborate, tetra(pintafluorophenyl)borate, and tetra(3, 5-bistrifluoromethylphenyl)borate, p-toluenesulfonate, or combinations thereof.

14. A method of photopolymerization comprising irradiating a photopolymerizable composition with actinic radiation until the photopolymerizable composition gels or hardens, said photopolymerizable composition comprising:

an ethylenically unsaturated monomer;

an arylsulfinate triarylsulfonium salt having an anion of Formula I $Ar^1—SO_2^-$    I and having a cation that is an triarylsulfonium ion, wherein $Ar^1$ is a substituted phenyl, an unsubstituted or substituted $C_{7-30}$ aryl, or an unsubstituted or substituted $C_{3-30}$ heteroaryl, said substituted $Ar^1$ having a substituent that is an electron withdrawing group or an electron withdrawing group in combination with an electron donating group, wherein the polymerizable composition generates a radical upon exposure to actinic radiation and wherein the polymerizable composition is free of an additive that competitively absorbs actinic radiation.

15. The method or claim 14, wherein the triarylsulfonium arylsulfinate salt has a cation according to Formula V

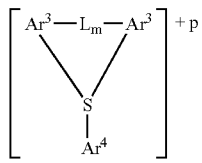

wherein each $Ar^3$ and $Ar^4$ are independently a $C_{6-30}$ aryl or a $C_{3-30}$ heteroaryl that is substituted or substituted with one or more substituents, each substituent having up to 30 carbon atoms and up to 10 heteroatoms selected from N, S, O, P, As, Si, Sb, B, or Ge; and L is a divalent linking group selected from a single bond, oxo, thio, sulfinyl, carbonyl, sulfonyl, methylene, or imino;

p in an interger equal to or greater than 1; and m is an interger equal to 0 or 1.

16. The method of claim 14, wherein the cation of the triarylsulfonium arylsulfinate is selected from

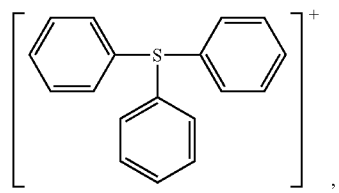

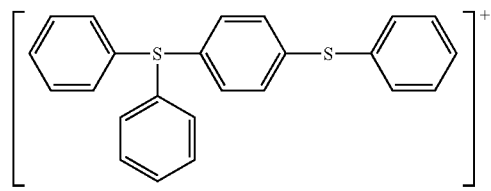

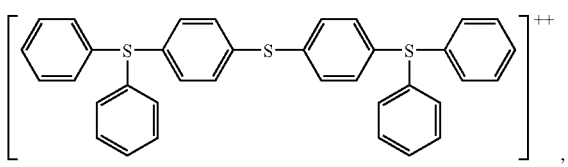

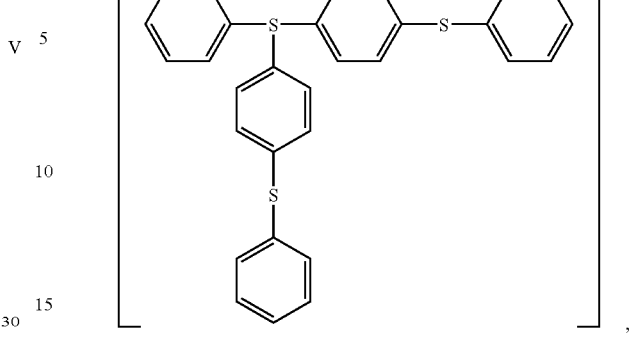

or combinations thereof that are unsubstituted or substituted with one or more substituents selected from alkyl, alkylcarbonyloxy, alkynyl, alkoxy, alkoxycarbonyl, alkylthio, arylthio, aralkyl, alkenyl, aryl, arylcarbonyloxy, arylcarbonylamido, alkylcarhonylamido, aryloxy, aryloxycarbonyl, alkoxysulfonyl, aryloxysulfonyl, alkysulfonamido, N-alkylaminocarbonyl, N-arylaminocarbonyl, N-alkylsulfamyl, N-arysulfamyl, alkylsulfonyl, arylsulonyl, perfluoralkyl, perfluoroalkysulfonyl, azo, boryl, halo, hydroxy, mercpto, diarylarsino, diarylstibino, trialkylgermano, trialkylsiloxy, or combinations thereof.

17. The method of claim 14, wherein the cation of the triarysulfonium arylsulfinate salt is triphenylsulfonium, diphenylnaphthylsulonium, tritolysulfonium, anisyldiphenylsulfonium, 4-butoxyphenyldipenylsulfonium, 4-tert-butylphenyldiphenylsulfonium, 4-chlorophenyldiphenylsulfonium, tris(4-phenoxyphenyl) sulfonium, 4-acetonylphenyldiphenylsulfonium, or tris(4-thiomethoxyphenyl)sulfonium, or 4-acetamidophenyldiphenylsulfonium.

18. The method of claim 14, wherein the triarylsulfonium arylsulfinate salt has an anion that is a beuzenesulfinate substituted with an electron withdrawing group selected from halo, cyano, fluoroakyl, perfluoroalky, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsufonyl, azo, alkenyl, alkynyl, dialylphosphonato, aminocarbonyl, or combinations thereof.

19. The method of claim 14, wherein the $Ar^1$ group of the trarylsulfonium arylsulfinate salt is naphthyl or anthraquinonyl that is unsubstituted or substituted with an electron withdrawing group or an electron withdrawing group in combination with an electron donating group.

20. The method of claim 14, wherein the actinic radiation is in the range of 250 to 1000 nanometers.

* * * * *

UNITED STATES PATENT AND TRADEMARK OFFICE
CERTIFICATE OF CORRECTION

PATENT NO. : 7,297,724 B2
APPLICATION NO. : 11/275831
DATED : November 20, 2007
INVENTOR(S) : Rajdeep S. Kalgutkar It is certified that error appears in the above-identified patent and that said Letters Patent is hereby corrected as shown below:

Title Page
Item [54], Delete "Photoiniators" and insert -- Photoinitiators --, therefor.

On the Title Page, item 56 Column 2, (Other Publications)
Line 5, Delete "Inititaion" and insert -- Initiation --, therefor.

Column 1
Line 50, Delete "abstract" and insert -- extract --, therefor.

Column 4
Line 43, Delete "a" and insert -- an --, therefor.
Line 62-63, Before "diarylphosphonato" delete "azo, alkenyl, alkynyl, dialkylphosphonato,". (Second Occurrence).

Column 9
Line 60, Delete "naphtyridinium" and insert -- naphthyridinium --, therefor.

Column 11
Line 15, Delete "methylbenxoxazolium" and insert -- methylbenzoxazolium --, therefor.
Line 31-32, Delete "1-anth-roquinonesulfinate" and insert -- 1-anthraquinonesulfinate --, therefor.

Column 13
Line 45, Delete "perfluoroalkysulfonyl" and insert -- perfluoroalkylsulfonyl --, therefor.
Line 58-59, Delete "4-butoxyphenyldipenylsulfonium," and insert -- 4-butoxyphenyldiphenylsulfonium, --, therefor.

Column 14
Line 55, Delete "divnylphthalate" and insert -- divinylphthalate --, therefor.

UNITED STATES PATENT AND TRADEMARK OFFICE
CERTIFICATE OF CORRECTION

PATENT NO.       : 7,297,724 B2
APPLICATION NO.  : 11/275831
DATED            : November 20, 2007
INVENTOR(S)      : Rajdeep S. Kalgutkar It is certified that error appears in the above-identified patent and that said Letters Patent is hereby corrected as shown below:

Column 16
Line 35 (approx.), Delete "methylbenxoxazolium" and insert
-- methylbenzoxazolium --, therefor.
Line 67, Delete "perfluoroalkysulfonyl" and insert
-- perfluoroalkylsulfonyl --, therefor.

Column 17
Line 51, Delete "perfluoroalkysulfonyl" and insert
-- perfluoroalkylsulfonyl --, therefor.

Column 19
Line 15, Delete "perfluoroalkysulfonyl" and insert -- perfluoroalkylsulfonyl --, therefor.
Line 67, Delete "perfluoroalkysulfonyl" and insert -- perfluoroalkylsulfonyl --, therefor.

Column 20
Line 43, After "Formual" insert -- . --.

Column 21
Line 53-54, Delete "perfluoroalkysulfonyl" and insert -- perfluoroalkylsulfonyl --, therefor.

Column 22
Line 40 (Approx.) Delete "perfluoroalkysulfonyl" and insert
-- perfluoroalkylsulfonyl --, therefor.
Line 44-45 (Approx.) After "cyanobenzenesulfinate," delete "triphenylsulfonium 4-cyanobenzenesulfinate,". (Second Occurrence)

Column 31
Line 67, In Claim 1, delete "on saturated" and insert -- unsaturated --, therefor.

UNITED STATES PATENT AND TRADEMARK OFFICE
CERTIFICATE OF CORRECTION

PATENT NO. : 7,297,724 B2
APPLICATION NO. : 11/275831
DATED : November 20, 2007
INVENTOR(S) : Rajdeep S. Kalgutkar It is certified that error appears in the above-identified patent and that said Letters Patent is hereby corrected as shown below:

Column 32
Line 6, In Claim 1, delete "$Ar^1$is" and insert -- $Ar^1$ is --, therefor. (Consider Space)
Line 7, In Claim 1, after "aryl" insert -- , --.
Line 24, In Claim 1, delete "front" and insert -- from --, therefor.
Line 27, In Claim 4, delete "perfluoroalkysulfonyl" and insert
-- perfluoroalkylsulfonyl --, therefor.
Line 28, In Claim 4, delete "alkenyl,alkynyl" and insert -- alkenyl, alkynyl --, therefor. (Consider Space)
Line 47, In Claim 6, delete "$R^1$is" and insert -- $R^1$ is --, therefor. (Consider Space)
Line 51, In Claim 6, delete "akyl" and insert -- alkyl --, therefor.
Line 51-52, In Claim 6, delete "unsubtituted" and insert -- unsubstituted --, therefor.
Line 55, In Claim 7, delete "tetralkylammonium" and insert -- tetraalkylammonium --, therefor.

Column 33
Line 32, In Claim 10, after "is" delete "substituted" and insert -- unsubstituted --, therefor.
Line 41, In Claim 10, after "m" delete "in".

Column 34
Line 22 (Approx.), In Claim 11, delete "arylithio" and insert -- arylthio --, therefor.
Line 24, In Claim 11, delete "alkysulfonamido" and insert -- alkylsulfonamido --, therefor.
Line 26, In Claim 11, delete "alkysulfonyl" and insert -- alkylsulfonyl --, therefor.
Line 27, In Claim 11, delete "perfluoroalkysulfonyl" and insert
-- perfluoroalkylsulfonyl --, therefor.
Line 28, In Claim 11, delete "diarystibino" and insert -- diarylstibino --, therefor.
Line 28, In Claim 11, delete "trialylgermano" and insert -- trialkylgermano --, therefor.
Line 28, In Claim 11, delete "trailkylsiloxy" and insert -- trialkylsiloxy --, therefor.
Line 31, In Claim 12, delete "triarylsufomium" and insert -- triarylsulfonium --, therefor.
Line 32-33, In Claim 12, delete "diphenylmaphthylsulfonium" and insert
-- diphenylnaphthylsulfonium --, therefor.
Line 34, In Claim 12, delete "4-butoxyphenyldipenylsulfonium" and insert
-- 4-butoxyphenyldiphenylsulfonium --, therefor.

UNITED STATES PATENT AND TRADEMARK OFFICE
CERTIFICATE OF CORRECTION

PATENT NO. : 7,297,724 B2
APPLICATION NO. : 11/275831
DATED : November 20, 2007
INVENTOR(S) : Rajdeep S. Kalgutkar It is certified that error appears in the above-identified patent and that said Letters Patent is hereby corrected as shown below:

Column 34
Line 34-35, In Claim 12, delete "4-tert-butylphenyldiphenylsulfonuim" and insert
-- 4-tert-butylphenyldiphenylsulfonium --, therefor.
Line 35, In Claim 12, delete "4-chlorophenyldiphenylsulfonuim" and insert
-- 4-chlorophenyldiphenylsulfonium --, therefor.
Line 35-36, In Claim 12, delete "tris(4-phenoxyphenyl)sulfonuim" and insert
-- tris(4-phenoxyphenyl)sulfonium --, therefor.
Line 37, In Claim 12, delete "tris(4-thiomethoxyphenyl)sulfonuim" and insert
-- tris(4-thiomethoxyphenyl)sulfonium --, therefor.
Line 41, In Claim 13, after "SbF6-," insert -- BF4-, --.
Line 43, In Claim 13, delete "tetra(pintafluorophenyl)borate" and insert
-- tetra(pentafluorophenyl)borate --, therefor.

Column 35
Line 1, In Claim 15, delete "or" and insert -- of --, therefor.
Line 17 (Approx.), In Claim 15, after "is" delete "substituted" and insert
-- unsubstituted --, therefor.
Line 25, In Claim 15, before "an" delete "in".
Line 25, In Claim 15, delete "interger" and insert -- integer --, therefor.
Line 26, In Claim 15, delete "interger" and insert -- integer --, therefor.

Column 36
Line 20-21, In Claim 16, delete "aryilthio" and insert -- arylthio --, therefor.
Line 22, In Claim 16, delete "alkylcarhonylamido," and insert
--alkylcarbonylamido, --, therefor.
Line 23, In Claim 16, delete "alkysulfonamido," and insert -- alkylsulfonamido, --,
therefor.
Line 25, In Claim 16, delete "N-arysulfamyl" and insert -- N-arylsulfamyl --, therefor.
Line 25, In Claim 16, delete "arylsulonyl" and insert -- arylsulfonyl --, therefor.
Line 26, In Claim 16, delete "perfluoroalkysulfonyl" and insert
-- perfluoroalkylsulfonyl --, therefor.
Line 26, In Claim 16, delete "mercpto" and insert -- mercapto --, therefor.
Line 30, In Claim 17, delete "triarysulfonium" and insert -- triarylsulfonium --, therefor.
Line 31, In Claim 17, delete "diphenylnaphthylsulonium" and insert
-- diphenylnaphthylsulfonium --, therefor.

UNITED STATES PATENT AND TRADEMARK OFFICE
CERTIFICATE OF CORRECTION

PATENT NO. : 7,297,724 B2
APPLICATION NO. : 11/275831
DATED : November 20, 2007
INVENTOR(S) : Rajdeep S. Kalgutkar It is certified that error appears in the above-identified patent and that said Letters Patent is hereby corrected as shown below:

Column 36
Line 32, In Claim 17, delete "4-butoxyphenyldipenylsulfonium" and insert
-- 4-butoxyphenyldiphenylsulfonium --, therefor.
Line 39, In Claim 18, delete "beuzenesulfinate" and insert -- benzenesulfinate --, therefor.
Line 41, In Claim 18, delete "fluoroakyl" and insert -- fluoroalkyl --, therefor.
Line 41, In Claim 18, delete "perfluoroalky" and insert -- perfluoroalkyl --, therefor.
Line 44, In Claim 18, delete "alkylsufonyl" and insert -- alkylsulfonyl --, therefor.
Line 44-45, In Claim 18, after "dialkylphosphonato," insert -- diarylphosphonato, --.
Line 47, In Claim 19, delete "trarylsulfonium" and insert -- triarylsulfonium --, therefor.

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,297,724 B2
APPLICATION NO. : 11/275831
DATED : November 20, 2007
INVENTOR(S) : Rajdeep S. Kalgutkar It is certified that error appears in the above-identified patent and that said Letters Patent is hereby corrected as shown below:

Title Page
Item [54] and Column 1, line 1, Delete "Photoiniators" and insert -- Photoinitiators --, therefor.

On the Title Page, item 56 Column 2, (Other Publications)
Line 5, Delete "Inititaion" and insert -- Initiation --, therefor.

Column 1
Line 50, Delete "abstract" and insert -- extract --, therefor.

Column 4
Line 43, Delete "a" and insert -- an --, therefor.
Line 62-63, Before "diarylphosphonato" delete "azo, alkenyl, alkynyl, dialkylphosphonato,". (Second Occurrence).

Column 9
Line 60, Delete "naphtyridinium" and insert -- naphthyridinium --, therefor.

Column 11
Line 15, Delete "methylbenxoxazolium" and insert -- methylbenzoxazolium --, therefor.
Line 31-32, Delete "1-anth-roquinonesulfinate" and insert -- 1-anthraquinonesulfinate --, therefor.

Column 13
Line 45, Delete "perfluoroalkysulfonyl" and insert -- perfluoroalkylsulfonyl --, therefor.
Line 58-59, Delete "4-butoxyphenyldipenylsulfonium," and insert -- 4-butoxyphenyldiphenylsulfonium, --, therefor.

Column 14
Line 55, Delete "divnylphthalate" and insert -- divinylphthalate --, therefor.

UNITED STATES PATENT AND TRADEMARK OFFICE
CERTIFICATE OF CORRECTION

PATENT NO. : 7,297,724 B2
APPLICATION NO. : 11/275831
DATED : November 20, 2007
INVENTOR(S) : Rajdeep S. Kalgutkar It is certified that error appears in the above-identified patent and that said Letters Patent is hereby corrected as shown below:

Column 16
Line 35 (approx.), Delete "methylbenxoxazolium" and insert
-- methylbenzoxazolium --, therefor.
Line 67, Delete "perfluoroalkysulfonyl" and insert
-- perfluoroalkylsulfonyl --, therefor.

Column 17
Line 51, Delete "perfluoroalkysulfonyl" and insert
-- perfluoroalkylsulfonyl --, therefor.

Column 19
Line 15, Delete "perfluoroalkysulfonyl" and insert -- perfluoroalkylsulfonyl --, therefor.
Line 67, Delete "perfluoroalkysulfonyl" and insert -- perfluoroalkylsulfonyl --, therefor.

Column 20
Line 43, After "Formual" insert -- . --.

Column 21
Line 53-54, Delete "perfluoroalkysulfonyl" and insert -- perfluoroalkylsulfonyl --, therefor.

Column 22
Line 40 (Approx.) Delete "perfluoroalkysulfonyl" and insert
-- perfluoroalkylsulfonyl --, therefor.
Line 44-45 (Approx.) After "cyanobenzenesulfinate," delete "triphenylsulfonium 4-cyanobenzenesulfinate,". (Second Occurrence)

Column 31
Line 67, In Claim 1, delete "on saturated" and insert -- unsaturated --, therefor.

UNITED STATES PATENT AND TRADEMARK OFFICE
CERTIFICATE OF CORRECTION

PATENT NO. : 7,297,724 B2
APPLICATION NO. : 11/275831
DATED : November 20, 2007
INVENTOR(S) : Rajdeep S. Kalgutkar It is certified that error appears in the above-identified patent and that said Letters Patent is hereby corrected as shown below:

Column 32
Line 6, In Claim 1, delete "$Ar^1$is" and insert -- $Ar^1$ is --, therefor. (Consider Space)
Line 7, In Claim 1, after "aryl" insert -- , --.
Line 24, In Claim 1, delete "front" and insert -- from --, therefor.
Line 27, In Claim 4, delete "perfluoroalkysulfonyl" and insert
-- perfluoroalkylsulfonyl --, therefor.
Line 28, In Claim 4, delete "alkenyl,alkynyl" and insert -- alkenyl, alkynyl --, therefor. (Consider Space)
Line 47, In Claim 6, delete "$R^1$is" and insert -- $R^1$ is --, therefor. (Consider Space)
Line 51, In Claim 6, delete "akyl" and insert -- alkyl --, therefor.
Line 51-52, In Claim 6, delete "unsubtituted" and insert -- unsubstituted --, therefor.
Line 55, In Claim 7, delete "tetralkylammonium" and insert -- tetraalkylammonium --, therefor.

Column 33
Line 32, In Claim 10, after "is" delete "substituted" and insert -- unsubstituted --, therefor.
Line 41, In Claim 10, after "m" delete "in".

Column 34
Line 22 (Approx.), In Claim 11, delete "arylithio" and insert -- arylthio --, therefor.
Line 24, In Claim 11, delete "alkysulfonamido" and insert -- alkylsulfonamido --, therefor.
Line 26, In Claim 11, delete "alkysulfonyl" and insert -- alkylsulfonyl --, therefor.
Line 27, In Claim 11, delete "perfluoroalkysulfonyl" and insert
-- perfluoroalkylsulfonyl --, therefor.
Line 28, In Claim 11, delete "diarystibino" and insert -- diarylstibino --, therefor.
Line 28, In Claim 11, delete "trialylgermano" and insert -- trialkylgermano --, therefor.
Line 28, In Claim 11, delete "trailkylsiloxy" and insert -- trialkylsiloxy --, therefor.
Line 31, In Claim 12, delete "triarylsufomium" and insert -- triarylsulfonium --, therefor.
Line 32-33, In Claim 12, delete "diphenylmaphthylsulfonium" and insert
-- diphenylnaphthylsulfonium --, therefor.
Line 34, In Claim 12, delete "4-butoxyphenyldipenylsulfonium" and insert
-- 4-butoxyphenyldiphenylsulfonium --, therefor.

UNITED STATES PATENT AND TRADEMARK OFFICE
CERTIFICATE OF CORRECTION

PATENT NO. : 7,297,724 B2
APPLICATION NO. : 11/275831
DATED : November 20, 2007
INVENTOR(S) : Rajdeep S. Kalgutkar It is certified that error appears in the above-identified patent and that said Letters Patent is hereby corrected as shown below:

Column 34
Line 34-35, In Claim 12, delete "4-tert-butylphenyldiphenylsulfonuim" and insert
-- 4-tert-butylphenyldiphenylsulfonium --, therefor.
Line 35, In Claim 12, delete "4-chlorophenyldiphenylsulfonuim" and insert
-- 4-chlorophenyldiphenylsulfonium --, therefor.
Line 35-36, In Claim 12, delete "tris(4-phenoxyphenyl)sulfonuim" and insert
-- tris(4-phenoxyphenyl)sulfonium --, therefor.
Line 37, In Claim 12, delete "tris(4-thiomethoxyphenyl)sulfonuim" and insert
-- tris(4-thiomethoxyphenyl)sulfonium --, therefor.
Line 41, In Claim 13, after "SbF6-," insert -- BF4-, --.
Line 43, In Claim 13, delete "tetra(pintafluorophenyl)borate" and insert
-- tetra(pentafluorophenyl)borate --, therefor.

Column 35
Line 1, In Claim 15, delete "or" and insert -- of --, therefor.
Line 17 (Approx.), In Claim 15, after "is" delete "substituted" and insert
-- unsubstituted --, therefor.
Line 25, In Claim 15, before "an" delete "in".
Line 25, In Claim 15, delete "interger" and insert -- integer --, therefor.
Line 26, In Claim 15, delete "interger" and insert -- integer --, therefor.

Column 36
Line 20-21, In Claim 16, delete "aryilthio" and insert -- arylthio --, therefor.
Line 22, In Claim 16, delete "alkylcarhonylamido," and insert
--alkylcarbonylamido, --, therefor.
Line 23, In Claim 16, delete "alkysulfonamido," and insert -- alkylsulfonamido, --,
therefor.
Line 25, In Claim 16, delete "N-arysulfamyl" and insert -- N-arylsulfamyl --, therefor.
Line 25, In Claim 16, delete "arylsulonyl" and insert -- arylsulfonyl --, therefor.
Line 26, In Claim 16, delete "perfluoroalkysulfonyl" and insert
-- perfluoroalkylsulfonyl --, therefor.
Line 26, In Claim 16, delete "mercpto" and insert -- mercapto --, therefor.
Line 30, In Claim 17, delete "triarysulfonium" and insert -- triarylsulfonium --, therefor.
Line 31, In Claim 17, delete "diphenylnaphthylsulonium" and insert
-- diphenylnaphthylsulfonium --, therefor.

UNITED STATES PATENT AND TRADEMARK OFFICE
CERTIFICATE OF CORRECTION

PATENT NO.        : 7,297,724 B2
APPLICATION NO. : 11/275831
DATED             : November 20, 2007
INVENTOR(S)       : Rajdeep S. Kalgutkar It is certified that error appears in the above-identified patent and that said Letters Patent is hereby corrected as shown below:

Column 36
Line 32, In Claim 17, delete "4-butoxyphenyldipenylsulfonium" and insert
-- 4-butoxyphenyldiphenylsulfonium --, therefor.
Line 39, In Claim 18, delete "beuzenesulfinate" and insert -- benzenesulfinate --, therefor.
Line 41, In Claim 18, delete "fluoroakyl" and insert -- fluoroalkyl --, therefor.
Line 41, In Claim 18, delete "perfluoroalky" and insert -- perfluoroalkyl --, therefor.
Line 44, In Claim 18, delete "alkylsufonyl" and insert -- alkylsulfonyl --, therefor.
Line 44-45, In Claim 18, after "dialkylphosphonato," insert -- diarylphosphonato, --.
Line 47, In Claim 19, delete "trarylsulfonium" and insert -- triarylsulfonium --, therefor.

This certificate supersedes the Certificate of Correction issued June 17, 2008.

Signed and Sealed this

Twenty-second Day of July, 2008

JON W. DUDAS
*Director of the United States Patent and Trademark Office*